(12) United States Patent
Ben-Shalom et al.

(10) Patent No.: US 10,523,054 B2
(45) Date of Patent: Dec. 31, 2019

(54) SYSTEM AND METHOD FOR TRIGGERING POWER TRANSFER ACROSS AN INDUCTIVE POWER COUPLING AND NON RESONANT TRANSMISSION

(71) Applicant: POWERMAT TECHNOLOGIES LTD., Neve Ilan (IL)

(72) Inventors: Amir Ben-Shalom, Modiin (IL); Oola Greenwald, Mevasseret Zion (IL); Arik Rofe, Jerusalem (IL); Asheri Moti, Jerusalem (IL); Elieser Mach, Rosh Tzurim (IL); Oz Moshkovich, Rehovot (IL); Guy Raveh, Mataa (IL)

(73) Assignee: POWERMAT TECHNOLOGIES LTD., Neve Ilan (IL)

( * ) Notice: Subject to any disclaimer, the term of this patent is extended or adjusted under 35 U.S.C. 154(b) by 873 days.

(21) Appl. No.: 15/146,363

(22) Filed: May 4, 2016

(65) Prior Publication Data

US 2016/0248280 A1    Aug. 25, 2016

Related U.S. Application Data

(63) Continuation of application No. 14/531,397, filed on Dec. 6, 2013, now Pat. No. 9,354,620, which is a
(Continued)

(51) Int. Cl.
*H02J 50/12* (2016.01)
*H02J 50/90* (2016.01)
(Continued)

(52) U.S. Cl.
CPC ............ *H02J 50/12* (2016.02); *A61N 1/3787* (2013.01); *G05B 13/0205* (2013.01);
(Continued)

(58) Field of Classification Search
CPC .... H02J 7/025; H02J 5/005; H02J 2007/0001; H01F 38/14
(Continued)

(56) References Cited

U.S. PATENT DOCUMENTS

| 2,212,414 A | 8/1940 | Burger |
| 7,164,255 B2 | 1/2007 | Hui |

(Continued)

FOREIGN PATENT DOCUMENTS

| EP | 1278402 A1 | 1/2003 |
| WO | 2014012060 A1 | 1/2014 |

OTHER PUBLICATIONS

Maxim Integrated Products; MAX8607—1MHz PWM Boost Converter for 1.5A White LED Camera Flash; Retrieved from the Internet: URL:http://datasheets.maximintegrated.com/en/ds/MAX8607.pdf; Feb. 2007; pp. 10; Sunnyvale, CA.
(Continued)

*Primary Examiner* — Alfonso Perez Borroto
(74) *Attorney, Agent, or Firm* — William Dippert; Laurence Greenberg; Werner Stemer

(57) ABSTRACT

A triggerable power transmitter for power transmission from a primary coil to an inductively coupled secondary coil in a power receiver has a primary coil; a driver for electrically driving the primary coil; a probing coil receives analog signals indicative of resonance properties of the primary coil; analog filters may be used to filter frequencies, and a processor capable of generating digital information in response to the analog signal and determining if said primary coil is coupled to a secondary coil based on the digital information, and triggering power from the primary coil to said secondary coil when said primary coil is inductively
(Continued)

coupled to said secondary coil. A resistor may be selectably connected in series with the primary coil and shorted out when power is transmitted.

8 Claims, 19 Drawing Sheets

Related U.S. Application Data continuation of application No. PCT/IL2013/050379, filed on May 2, 2013.

(60) Provisional application No. 61/642,165, filed on May 3, 2012, provisional application No. 61/650,683, filed on May 23, 2012.

(51) Int. Cl.
| | |
|---|---|
| *H02J 50/60* | (2016.01) |
| *H04B 5/00* | (2006.01) |
| *A61N 1/378* | (2006.01) |
| *G05B 13/02* | (2006.01) |
| *H02J 50/80* | (2016.01) |

(52) U.S. Cl.
CPC .............. *H02J 50/60* (2016.02); *H02J 50/80* (2016.02); *H02J 50/90* (2016.02); *H04B 5/0037* (2013.01); *H04B 5/0093* (2013.01)

(58) Field of Classification Search
USPC .......................................... 307/104; 320/108
See application file for complete search history.

(56) References Cited

U.S. PATENT DOCUMENTS

| | | | |
|---|---|---|---|
| 8,884,561 B2 | 11/2014 | Widmer | B60L 11/182 320/104 |
| 8,952,654 B2 | 2/2015 | Uramoto | H02J 7/0027 320/108 |
| 2008/0079371 A1 | 4/2008 | Kang et al. | |
| 2009/0010028 A1 | 1/2009 | Baarman | H02J 5/005 363/25 |
| 2009/0243394 A1 | 10/2009 | Levine | H02J 5/005 307/104 |
| 2010/0072825 A1 | 3/2010 | Azancot et al. | |
| 2010/0084918 A1* | 4/2010 | Fells | H02J 5/005 307/32 |
| 2010/0117596 A1 | 5/2010 | Cook | B60L 11/182 320/108 |
| 2011/0004278 A1 | 1/2011 | Aghassian | A61N 1/3787 607/61 |
| 2012/0112691 A1* | 5/2012 | Kurs | B60L 11/182 320/108 |

OTHER PUBLICATIONS

International Search Report for the corresponding International Application No. PCT/US2013/050379 dated Nov. 10, 2013.
International Preliminary Report on Patentability for the corresponding International Application No. PCT/US2013/050379 dated Jan. 13, 2015.

* cited by examiner

SYSTEM AND METHOD FOR TRIGGERING POWER TRANSFER ACROSS AN INDUCTIVE POWER COUPLING AND NON RESONANT TRANSMISSION

CROSS-REFERENCE TO RELATED APPLICATIONS

This application is a continuation of U.S. patent application Ser. No. 14/531,397, filed Dec. 6, 2013, which in turn is a continuation of International Patent Application No. PCT/IL2013/050379, filed May 2, 2013, which is based upon and claims the benefit of U.S. Provisional Patent Application Ser. No. 61/642,165, filed May 3, 2012, and Ser. No. 61/650,683 filed May 23, 2012, the disclosures of which are hereby incorporated by reference in their entirety herein.

FIELD OF THE DISCLOSURE

The disclosure herein is directed to providing devices, a system and method for triggering and controlling power transfer across an inductive power coupling. The disclosure further provides a communications channel for the transfer of feedback signals in inductive power transfer systems. More specifically, the present disclosure relates to coil-to-coil signal transfer in inductive power couplings.

BACKGROUND OF THE INVENTION

Inductive power coupling allows energy to be transferred from a power supply to an electric load without a wired connection therebetween. A power supply is wired to a primary coil and an oscillating electric potential is applied across the primary coil which induces an oscillating magnetic field therearound. The oscillating magnetic field may induce an oscillating electrical current in a secondary coil, placed close to the primary coil. In this way, electrical energy may be transmitted from the primary coil to the secondary coil by electromagnetic induction without the two coils being conductively connected.

When electrical energy is transferred from a primary inductor to a secondary inductor, the inductors are said to be inductively coupled. An electric load wired in series with such a secondary inductor may draw energy from the power source wired to the primary inductor when the secondary inductor is inductively coupled thereto.

For safety, the power supplying side of a conductive couple is generally the female part, and does not have bare conductive elements protruding therefrom. Nevertheless, socket holes are dangerous and children do sometimes manage to insert pencils, pins and other objects into socket holes, sometimes with fatal results. Water can also cause shorting and may result in electrocution.

It can therefore be safer and more reliable to provide socket-less power outlets such as inductive couplers. Inductive power coupling allows energy to be transferred from a power supply to an electric load without connecting wires, as detailed hereinabove.

Low power inductive electrical power transmission systems over extended surfaces are not new. One such example is described in U.S. Pat. No. 7,164,255 to Hui. In Hui's system a planar inductive battery charging system is designed to enable electronic devices to be recharged. The system includes a planar charging module having a charging surface on which a device to be recharged is placed. Within the charging module, and parallel to the charging surface, at least one, and preferably an array of primary windings are provided. These couple energy inductively to a secondary winding formed in the device to be recharged. Such systems are adequate for charging batteries in that they typically provide a relatively low power inductive coupling. It will be appreciated however, that extended base units such as Hui's charging surface which transmit energy continually approximately uniformly over the whole area of the unit, are not suitable for use with high energy systems.

United States Patent Application 2010/0072825, to Azancot et. al. discloses a system and method for controlling power transfer across an inductive power coupling. The application discloses a signal transfer system for controlling power transfer across an inductive power coupling. A transmission circuit associated with an inductive power receiver is configured to transmit a control signal to a reception circuit associated with an inductive power outlet. The signal transfer system may be used to regulate the power supplied by the inductive coupling and to detect the presence of the secondary coil.

It is noted that that the strength of the induced voltage in the secondary inductor varies according to the oscillating frequency of the electrical potential provided to the primary inductor. The induced voltage is strongest when the oscillating frequency equals the resonant frequency of the system. The resonant frequency $f_R$ depends upon the inductance L and the capacitance C of the system according to the equation $$f_R = \frac{1}{2\pi\sqrt{LC}}.$$

It is further noted that known inductive power transfer systems typically transmit power at the resonant frequency of the inductive couple. This can be difficult to maintain as the resonant frequency of the system may fluctuate during power transmission, for example in response to changing environmental conditions or variations in alignment between primary and secondary coils.

Therefore, inductive transfer systems designed to transmit at resonance require tuning mechanisms for maintaining transmission at the resonant frequency of the system. Tuning may be achieved by adjusting the driving frequency to seek resonance. For example, U.S. Pat. No. 6,825,620, titled "Inductively coupled ballast circuit" to Kuennen et al. describes a resonance seeking ballast circuit for inductively providing power to a load. The ballast circuit includes an oscillator, a driver, a switching circuit, a resonant tank circuit and a current sensing circuit. The current sensing circuit provides a current feedback signal to the oscillator that is representative of the current in the resonant tank circuit. The current feedback signal drives the frequency of the ballast circuit causing the ballast circuit to seek resonance. The ballast circuit includes a current limit circuit that is inductively coupled to the resonant tank circuit. The current limit circuit disables the ballast circuit when the current in the ballast circuit exceeds a predetermined threshold or falls outside a predetermined range.

Alternatively, tuning may be achieved by adjusting the characteristics of the inductive system. For example, U.S. Pat. No. 2,212,414, titled "Adaptive inductive power supply" to Baarman describes a contactless power supply which has a dynamically configurable tank circuit powered by an inverter. The contactless power supply is inductively coupled to one or more loads. The inverter is connected to a DC power source. When loads are added or removed from the system, the contactless power supply is capable of modifying the resonant frequency of the tank circuit, the inverter frequency, the inverter duty cycle or the rail voltage of the DC power source.

Tuning mechanisms such as those described above are necessary in order to maintain transmission at resonance because resonant transmission is highly sensitive. At resonance small variations to the system result in large changes to the power transferred. A further problem associated with resonant transmission is the high transmission voltages involved. At high operating voltages, the capacitors and transistors in the circuit need to be relatively large.

There is a need for an inductive transfer system with a higher tolerance to environmental fluctuations and variations in inductive coil alignment and which transmits at low voltages. The present invention addresses this need.

SUMMARY OF THE INVENTION

It is an aspect of the current disclosure to provide a method of triggering power transmission in inductively coupled power transmission system comprising: a. waiting a time duration; b. electrically exciting a primary coil in a power transmitter; c. receiving a signal indicative of resonance properties of the primary coil; d. determining if a secondary coil in a power receiver is inductively coupled to the primary coil; and e. triggering power transmission from the primary coil to said secondary coil if the secondary coil is inductively coupled to the primary coil, or repeating steps a-d if the secondary coil is not inductively coupled to the primary coil.

In some embodiments exciting of the primary coil in a power transmitter comprises applying a short electric pulse to the primary coil.

In some embodiments determining if the secondary coil is inductively coupled to the primary coil comprises determining a change in resonance frequency of the primary coil.

In some embodiments determining if the secondary coil is inductively coupled to said primary coil comprises determining that the change in resonance frequency of said primary coil is a reduction of the resonance frequency.

In some embodiments determining if the secondary coil is inductively coupled to the primary coil comprises determining a change in effective inductance of the primary coil.

In some embodiments determining if the secondary coil is inductively coupled to the primary coil further comprises determining a change in effective resistance of the primary coil.

In some embodiments determining if the secondary coil is inductively coupled to the primary coil comprises determining a match between: values indicative of effective inductance of the primary coil; and values indicative of effective resistance of the primary coil to at least one set of values associated with the primary coil inductively coupled to the secondary coil.

In some embodiments determining if the secondary coil is inductively coupled to the primary coil comprises determining a match between: values indicative of effective inductance of the primary coil; and values indicative of effective resistance of the primary coil to at least one set of values in a list of values associated with a primary coil inductively coupled to a plurality of different types of power receivers.

In some embodiments, triggering power transmission from the primary coil to the secondary coil if the secondary coil is inductively coupled to the primary coil comprises controlling the power transmission according to type of a power receiver associated with the matched values indicative of effective inductance of the primary coil; and values indicative of effective resistance of the primary coil.

In some embodiments repeating steps a-d if the secondary coil is not inductively coupled to the primary coil further comprising issuing a warning if the signal indicative of resonance properties of the primary coil indicates that an object other than the secondary coil is inductively coupled to the primary coil.

In some embodiments exciting of a primary coil in a power transmitter comprises short duration activation of a driver used for driving the primary coil during power transmission from the primary coil to the secondary coil.

In some embodiments exciting of the primary coil in a power transmitter comprises activation of the driver used for driving the primary coil during power transmission from the primary coil to the secondary coil at power level significantly reduced compared to power levels used for driving the primary coil during power transmission.

In some embodiments exciting of the primary coil in the power transmitter at reduced power level comprising exciting the primary coil at a plurality of frequencies, and determining if the secondary coil in the power receiver is inductively coupled to the primary coil comprises assessing frequency response of the primary coil.

It is another aspect of the disclosure to provide a triggerable power transmitter for power transmission from a primary coil in the power transmitter to an inductively coupled secondary coil in a power receiver comprising: a primary coil, capable of being inductively coupled to a secondary coil in a power receiver; a driver, capable of electrically driving the primary coil; a front end, capable of receiving analog signal indicative of resonance properties of the primary coil and capable of generating digital information in response to the analog signal; and a processor, receiving the digital information and capable of: determining if the primary coil is coupled to a secondary coil based on the digital information, and controlling the driver to transmit power from the primary coil to the secondary coil when the primary coil is inductively coupled to the secondary coil.

In some embodiments the front end is connected to the primary coil.

In some embodiments the transmitter further comprises a probing coil; the probing coil is capable of providing the front end with analog signal indicative of resonance properties of the primary coil.

In some embodiments the transmitter further comprises a resistor, placed in series to primary coil and capable of providing the front end with analog signal indicative of resonance properties of the primary coil.

In some embodiments the transmitter further comprises a switch placed in parallel to the resistor and capable of shorting out the resistor when power is transmitted from the primary coil to the secondary coil.

In some embodiments the transmitter further comprises a plurality of alignment coils capable of providing signals indicative of misalignment of the secondary coil in relation to the primary coil.

It is noted that some embodiments of the present disclosure are further directed towards providing an inductive power transfer system adapted to transmit power at a non-resonant frequency comprising at least one inductive power outlet comprising at least one primary inductive coil wired to a power supply via a driver, wherein the at least one primary inductive coil associated with an inductive power receiver; and a remote secondary unit comprising at least one secondary inductive coil wired to an electric load, the at least one secondary inductive coil associated with an inductive power transmitter; wherein the at least one primary inductive coil is configured to form an inductive couple with the at least one secondary inductive coil and wherein the driver is configured to provide a driving voltage across the primary inductive coil, the driving voltage oscillating at a transmission frequency significantly different from the resonant frequency of the inductive couple. Optionally, the driver comprises a switching unit for intermittently connecting the primary inductive coil to the power supply.

The inductive power transfer system further comprising an inductive feedback channel for transferring signals concurrently with uninterrupted inductive power transfer between the inductive power transmitter and the inductive power receiver.

Where appropriate, the transmission frequency may lie within a range in which induced voltage varies approximately linearly with frequency. Optionally, the driver is configured to adjust the transmission frequency in response to feedback signals.

Optionally, the inductive power outlet comprises a signal detector adapted to detect a first signal and a second signal, and the driver is configured to: increase the transmission frequency when the first signal is detected by the detector, and decrease the transmission frequency when the second signal is detected by the detector. The feedback signals generally carry data pertaining to the operational parameters of the electric load. Operational parameters are selected from the group comprising: required operating voltage for the electric load; required operating current for the electric load; required operating temperature for the electric load; required operating power for the electric load; measured operating voltage for the electric load; measured operating current for the electric load; measured operating temperature for the electric load; measured operating power for the electric load; power delivered to the primary inductive coil; power received by the secondary inductive coil, and a user identification code. Optionally, the detector is selected from the list comprising optical detectors, radio receivers, audio detectors and voltage peak detectors.

Optionally, the driver further comprises a voltage monitor for monitoring the amplitude of a primary voltage across the primary coil. Optionally, the voltage monitor is configured to detect significant increases in primary voltage.

In some cases, the driving voltage oscillating at a transmission frequency higher than the resonant frequency of the inductive couple, wherein the primary inductive coil is further wired to a reception circuit comprising a voltage monitor for monitoring the amplitude of a primary voltage across the primary coil, and the secondary inductive coil is further wired to a transmission circuit for connecting at least one electric element to the secondary inductive coil thereby altering the resonant frequency such that a control signal may be transferred from the transmission circuit to the reception circuit. Variously, the resonance altering electric element may include a capacitor configured to connect to the secondary inductive coil either in parallel or series and thereby to effectively increase or decrease the resonant frequency of the system. Alternatively or additionally, the resonance altering electric element may include an inductor configured to connect to the secondary inductive coil either in parallel or series and thereby to effectively increase or decrease the resonant frequency of the system. Still further, the resonance altering electric element may be damping element such as a resistor, capacitor, inductor or the like operable to connect to the secondary inductor thereby damping the resonance and effectively increasing the resonant frequency of the system. Alternatively damping may be reduced, for example by adding damping elements such as resistors in parallel to extant damping elements or disconnecting extant damping elements from the secondary inductor.

Optionally, the secondary inductive coil is wired to two inputs of a bridge rectifier and the electric load is wired to two outputs of the bridge rectifier wherein the transmission circuit is wired to one input of the bridge rectifier and one output of the bridge rectifier. Typically, the transmission circuit further comprises a modulator for modulating a bit-rate signal with an input signal to create a modulated signal and a switch for intermittently connecting the electrical element to the secondary inductive coil according to the modulated signal. Optionally, the voltage monitor further comprises a correlator for cross-correlating the amplitude of the primary voltage with the bit-rate signal for producing an output signal.

In certain embodiments, the control signal is usable for transferring a feedback signal from the secondary inductive coil to the primary inductive coil for regulating power transfer across an inductive power coupling. The driver may be configured to adjust the transmission frequency in response to the feedback signals. Accordingly, the system may be adapted to transfer a first signal and a second signal, and the driver is configured to: increase the transmission frequency when the first signal is received by the receiver, and decrease the transmission frequency when the second signal is received by the receiver.

In an alternative embodiment of the inductive power transfer system, the inductive feedback channel may comprise a transmission circuit incorporated in the secondary unit and a receiving circuit incorporated in the inductive power outlet.

The inductive feedback channel may further comprise at least one auxiliary coil operable to detect fluctuations in the magnetic field in the vicinity of the primary inductor and of the at least one secondary inductor to pick up feedback signals.

Optionally, the at least one auxiliary coil may be connected to the receiving circuit configured to produce output signals based on the magnetic fluctuations.

Optionally, the output signals may be transmission parameters configured to adjust transmission frequency.

Additionally or alternatively, the output signals may include operational parameters configured to provide data instructions to the receiving circuit.

Optionally, the auxiliary coil comprises an external coil to provide filtering.

Where required, one or more auxiliary coils may be incorporated into the transmission circuit.

Variously, the system may be incorporated into at least one application selected from a group consisting of: inductive chargers, inductive power adaptors, power tools, kitchen appliances, bathroom appliances, computers, media players, office equipment, implanted devices, pace makers, trackers and RFID tags inductive chargers, inductive power adaptors.

Furthermore the current disclosure teaches a method for regulating power transmission inductive from a primary inductive coil, wired to a power supply via a driver, to a secondary inductive coil, wired to an electric load, the method comprising the following steps: (a)—providing an oscillating voltage to the primary inductive coil at an initial transmission frequency ft which is substantially different from the resonant frequency $f_R$ of the system; (b)—inducing a secondary voltage in the secondary inductive coil; (c)—monitoring power received by the electric load; (d)—sending a feedback signal when the monitored power deviates from a predetermined range; (e)—the driver receiving the feedback signal; (f)—the driver adjusting the transmission frequency; and (g)—repeating steps (b)-(f).

Optionally, step (d) further comprises: (d1) sending a feedback signal of a first type $S_a$ to the driver, whenever the power drops below a predetermined lower threshold, and (d2) sending a feedback signal of a second type $S_b$ to the driver, whenever the power exceeds a predetermined upper threshold.

Optionally, the initial transmission frequency $f_t$ is higher than the resonant frequency $f_R$ and step (f) further comprises: (f1) the driver reducing the transmission frequency by an incremental value $-\delta f_1$ when the received feedback signal is of the first type $S_a$, and (f2) the driver increasing the transmission frequency by an incremental value $+\delta f_2$ when the received feedback signal is of the second type $S_b$.

In still other embodiments, the invention is directed to teaching another method for transferring a signal from a secondary inductive coil to a primary inductive coil of an inductive power transfer system, said method comprising the following steps: Step (i)—connecting the primary inductive coil to a voltage monitor for monitoring the amplitude of a primary voltage across the primary coil; Step (ii)—connecting the secondary inductive coil to a transmission circuit for selectively increasing the resonant frequency of the inductive power transfer system; Step (iii)—providing an oscillating voltage to the primary inductive coil at an initial transmission frequency higher than the resonant frequency thereby inducing a voltage in the secondary inductive coil; Step (iv)—using the transmission circuit to modulate a bit-rate signal with the input signal to create a modulated signal and connecting a electrical element to the secondary inductive coil intermittently according to the modulated signal, and Step (v)—using the voltage monitor to cross-correlate the amplitude of the primary voltage with the bit-rate signal for producing an output signal.

Variously, the resonance altering electrical element may include a capacitor configured to connect to the secondary inductive coil either in parallel or series and thereby to effectively increase or decrease the resonant frequency of the system. Alternatively or additionally, the resonance altering electrical element may include an inductor configured to connect to the secondary inductive coil either in parallel or series and thereby to effectively increase or decrease the resonant frequency of the system. Still further, the resonance altering electrical element may be damping element such as a resistor, capacitor, inductor or the like operable to connect to the secondary inductor thereby damping the resonance and effectively increasing the resonant frequency of the system. Alternatively damping may be reduced, for example by adding damping elements such as resistors in parallel to extant damping elements or disconnecting extant damping elements from the secondary inductor.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE FIGURES

For a better understanding of the invention and to show how it may be carried into effect, reference will now be made, purely by way of example, to the accompanying drawings.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention; the description taken with the drawings making apparent to those skilled in the art how the several forms of the invention may be embodied in practice. In the accompanying drawings.

DETAILED DESCRIPTION OF THE INVENTION

Figure 1:
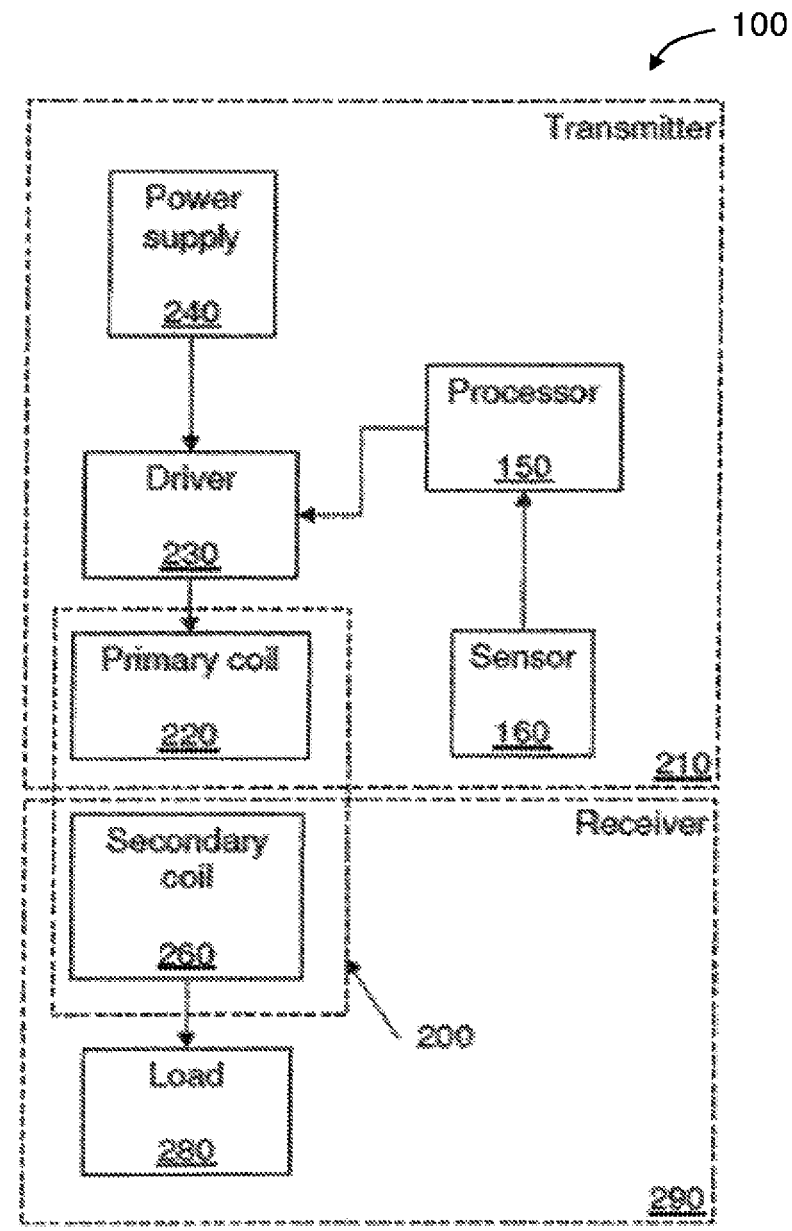
FIG. 1 schematically depicts a block diagram of the main elements of an inductive power transfer system as known in the art.

As required, detailed embodiments of the present disclosure are disclosed herein; however, it is to be understood that the disclosed embodiments are provided merely as illustrative of the disclosure that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present disclosure.

Before explaining at least one embodiment of the disclosure in detail, it is to be understood that the disclosure is not necessarily limited in its application to the details set forth in the following description or exemplified by the Examples. The disclosure is capable of other embodiments or of being practiced or carried out in various ways.

The terms "comprises", "comprising", "includes", "including", and "having" together with their conjugates mean "including but not limited to". The term "consisting of" has the same meaning as "including and limited to". The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

In discussion of the various figures described herein below, like numbers refer to like parts. The drawings are generally not to scale. For clarity, non-essential elements were omitted from some of the drawing. Reference is now made to the drawings.

FIG. 1 schematically depicts a block diagram of the main elements of an inductive power transfer system 100 as known in the art.

The inductive power coupling 200 consists of a primary inductive coil 220 and a secondary inductive coil 260. The primary coil 220 is wired to a power supply 240, typically via a driver 230 which provides the electronics necessary to drive the primary coil 220. Driving electronics may include a switching unit providing a high frequency oscillating voltage supply, for example. The secondary coil 260 is wired to an electric load 280. For drawing clarity, internal details of load 280 are not seen in this and the following figures. It should be noted that load 280 may comprise rectification and other electronic circuitry. For example, for battery charging application, load 280 may represent a rechargeable battery, an AC to DC rectification, and optionally at least one of: a DC to DC power conditioning circuits, battery charging regulation functions, and means of communication with transmitter 210 in order to regulate power transmission to meet the power requirements of the battery charger, and optionally to terminate power transmission when battery is fully charged.

When the secondary coil 260 is brought into proximity with the primary coil 220, the pair of coils forms an inductive couple and power is transferred from the primary coil 220 to the secondary coil 260. In this way a power transmitter 210 may provide power to an electric receiver device 290.

However, it is important to activate the power transmission only when the secondary coil 260 is present, and correctly aligned with the primary coil 220. Activation of power transmission without proper placement of the power receiver 290 may cause electromagnetic waves radiating from the primary coil 220 to leak into the environment, possibly causing energy loss, electromagnetic interference, and health risk.

A sensor 160 is used for detecting the presence of receiver 290 and signaling processor 150 to activate driver 230 to start activating primary coil 220 only when receiver 290 is detected.

It should be noted that typically inductive power transfer system 100 may stand idle for much of the time, and is activated infrequently and for some limited time duration. Such is the case wherein inductive power transfer system 100 is used for example recharging a cellular phone and the likes. To reduce energy consumption, the system should remain in low power consumption state before detecting the presence of receiver 290.

Processor 150 is optionally used for controlling other functions of system 100, for example it may be used for regulating power transmission according to the power requirements of load 280. Optionally, processor 150 further terminates power transmission, for example when a rechargeable battery in load 280 is fully charged.

Additionally, it is important that the inductive coupling 200 between primary coil 220 and secondary coil 260 is not interrupted by foreign material that may be placed between the transmitter 210 and the receiver 290. For example even a thin layer of conductive material such as metal foil may absorb enough of the transmitted electrical power to produce heat, thus creating fire hazard.

Several types of sensors 160 may be used, these include for example: magnetic sensors such as Hall Effect sensors that detects changes in magnetic field caused by magnetic material at the receiver; audio sensors such as a microphone capable of detecting vibration caused by placing the receiver on the transmitter, capacitive sensors; weight detection, mechanical switch and others.

Figure 2:
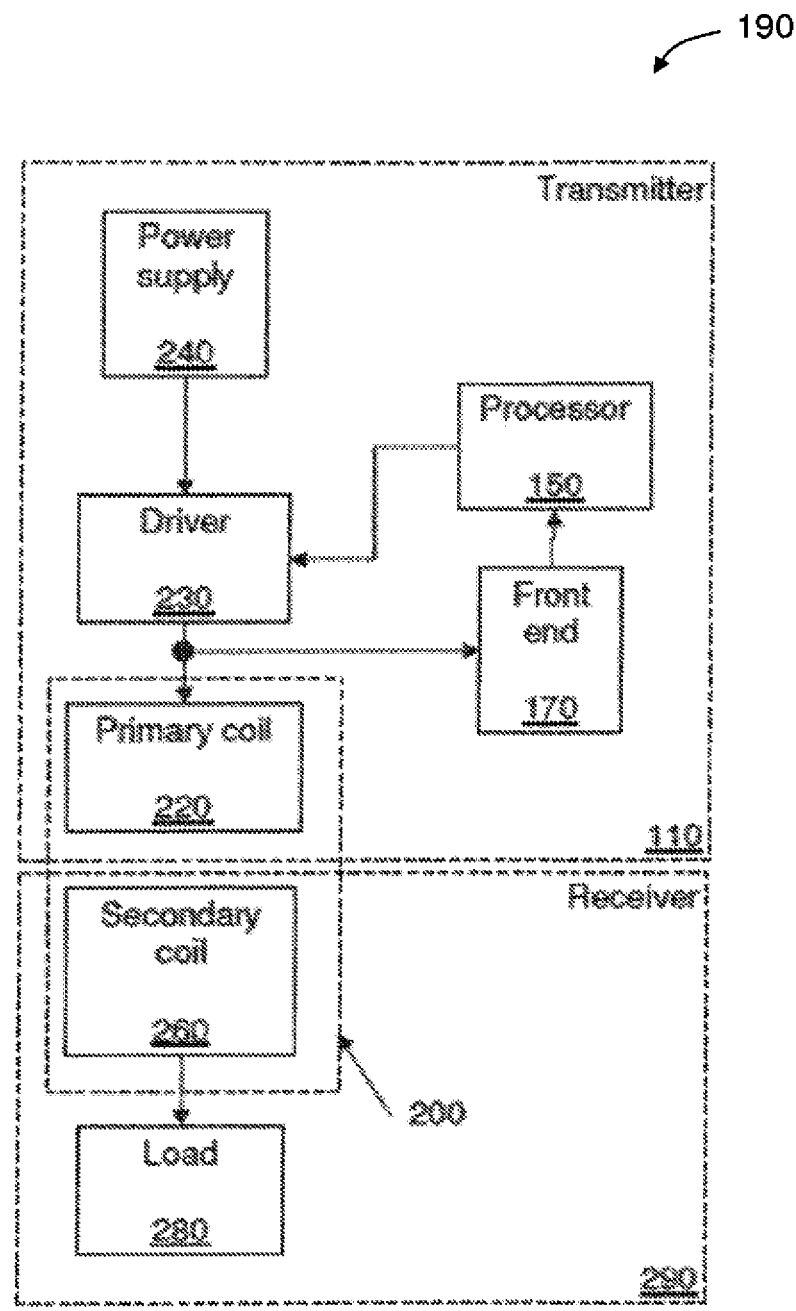
FIG. 2 schematically depicts a block diagram of the main elements of an inductive power transfer system according to an exemplary embodiment of the current invention.

FIG. 2 schematically depicts a block diagram of the main elements of an inductive power transfer system 190 according to an exemplary embodiment of the current invention.

It is one system the primary coil 22 may be used as a sensor for sensing the presence of the receiver 290 instead of using sensor 160.

In the example of FIG. 2, primary coil 220 is connected to front end electronics 170 which is capable of sensing changes in the inductance of primary coil 22 due its inductive coupling 200 to secondary coil 260.

Primary coil 220 may be a part of a resonance circuit having a resonance frequency according to the inductance and capacitance in said circuit. When the inductance in the circuit changes the resonance frequency changes accordingly. The change in resonance frequency may be used as an indication that a secondary coil 260 is coupled to primary coil 220, thus triggering power transfer from transmitter 110 to receiver 290.

The new resonance frequency may be used for assessing the quality of the coupling 200 between primary coil 220 and secondary coil 260. This information may be used for indication to the user of the system 190 to correct poor alignment or incorrect placement of receiver 290. Furthermore, the measured resonant frequency may be used to determine the required transmission frequency of the system.

Figure 3:
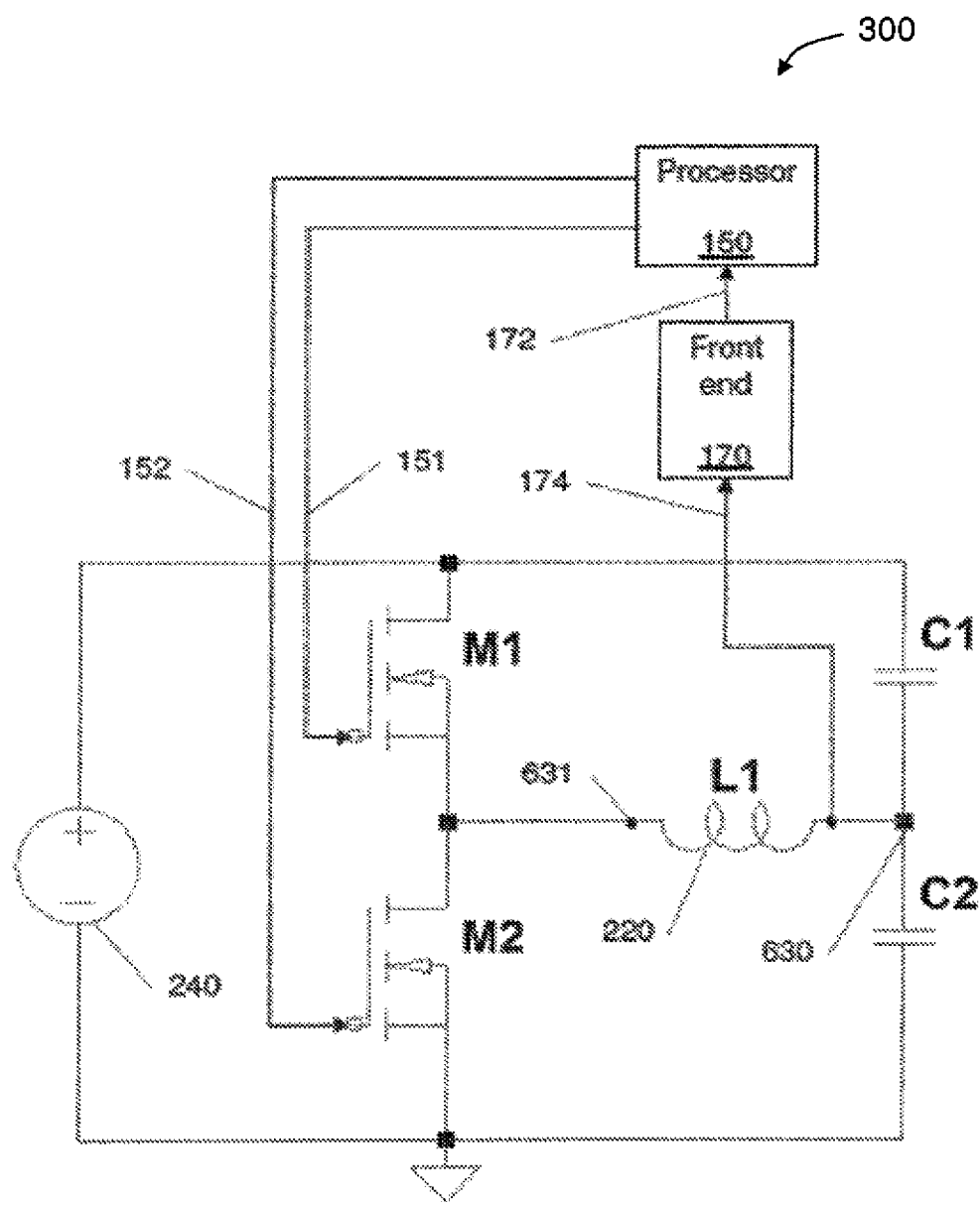
FIG. 3 schematically depicts an electrical circuitry according to an exemplary embodiment of the current invention.

FIG. 3 schematically depicts an electrical circuitry 300 according which may be used in the power transmission system.

Electrical circuit 300 shows a DC power supply 240 connected to an AC driver comprising FET switches M1 and M1 and to a resonance circuit comprising the primary coil 220 and capacitors C1 and C2.

In power transmission mode, switches M1 and M2 are sequentially activated by gating signals 151 and 152 respectively, causing AC current to flow through primary coil 220 which induces generation of voltage in the inductively coupled secondary coil 260. For drawing clarity elements not needed for the understanding of the operation of the circuit were omitted.

Primary coil 220 is connected to front end 170, for example via line 174 connected to terminal 630 of coil 220 which senses the voltage on the coil and provides processor 150 with signals 172 indicative of the changes in electrical properties of the resonance circuit caused by the proximity of the receiver 290. Additionally or alternatively, front end 170 may be connected to the other terminal 631 of coil 220. Alternatively, front end 170 may be connected to both terminals, sensing the voltage difference between terminals 630 and 631. Alternatively, front end 170 may be connected to some partial number of the windings of primary coil 220.

Figure 4:
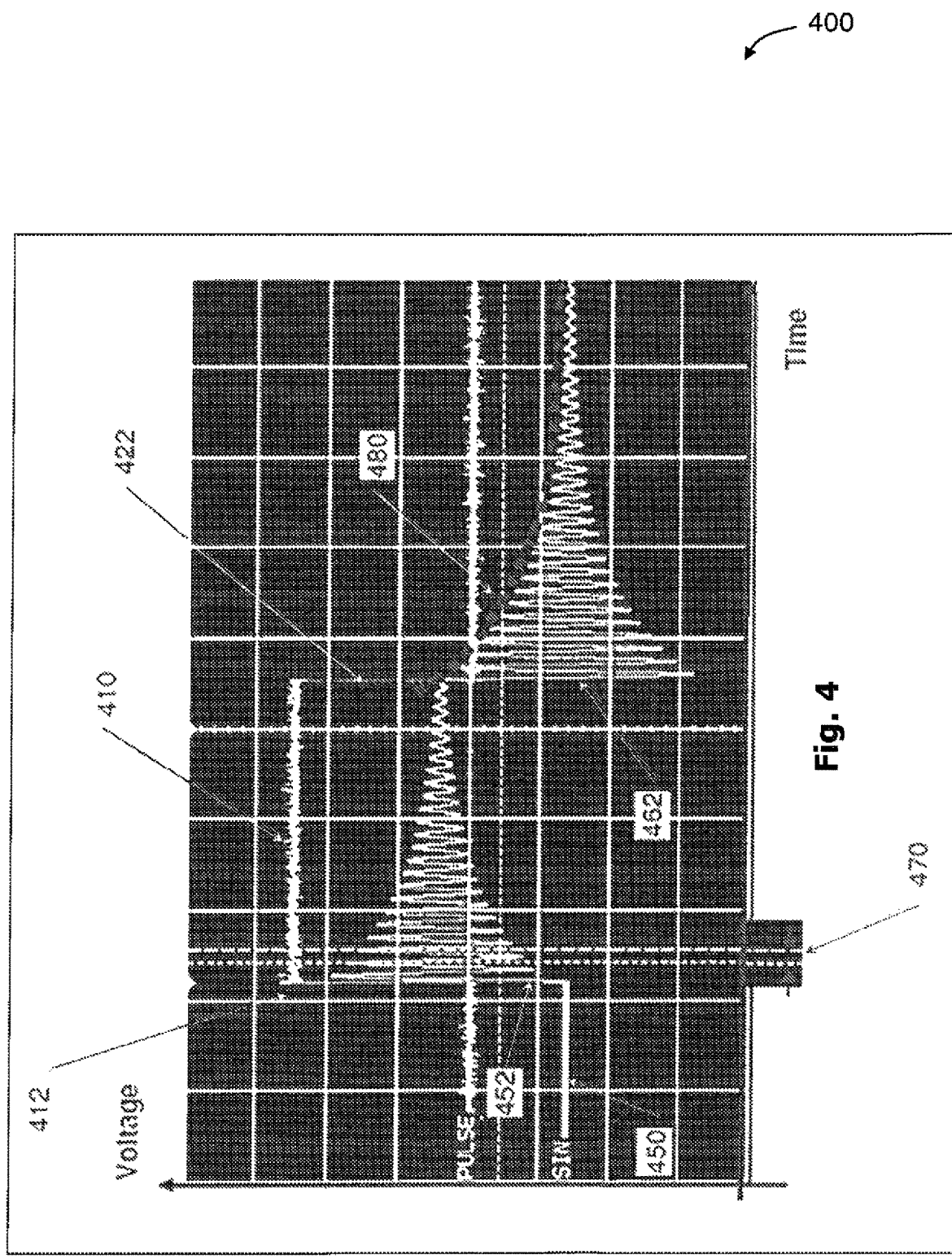
FIG. 4 schematically depicts experimental results from a setup equivalent to circuit 300 wherein front end unit was replaced with an oscilloscope.

FIG. 4 schematically depicts experimental results from a setup equivalent to circuit 300 wherein front end 170 was replaced with an oscilloscope.

Graph 400 shows two traces: Trace 410 shows the voltage on gating signal 151 while trace 450 is the voltage 174 on primary coil 220.

At point 412 of trace 410, gate signal 151 goes from "zero" to "one" closing switch M1 while switch M2 is open. This causes a rise 452 in voltage 174 as indicated by the rise of trace 450. The current on primary coil 220 start to oscillate at the resonance frequency given by the effective values of the inductive L1 of coil 220 and the equivalent capacitance (approximately given by the sum of capacitance C1+C2, but may be effected by other stray and real capacitance not seen in this figure) in the resonance circuit. In the absence of load, the oscillations decay due to losses in the resonance circuit, for example due to Ohmic resistance of coil 220 and energy dissipation due to electromagnetic waves radiated by the coil.

At point 422 of trace 410, gate signal 151 goes from "one" to "zero" opening switch M1 while switch M2 closes. This causes a fall 462 in voltage 174 as indicated by the fall of trace 450.

It should be noted that the oscillations of the current in primary coil 220 are caused by the pulsed nature of the excitation caused by the closing and opening of switches M1 and M2. Resonance frequency may be determined for example by measuring the time interval 470 taken for one oscillation. The decay envelop 480 of oscillations of trace 450 is indicative of the losses in the resonance circuit.

After a pulsed excitation, and in absence of appreciable load, the current in the primary coil oscillate at the resonance frequency f given by:

$$f = \frac{1}{2\pi}\sqrt{\frac{1}{LC} - \left(\frac{R}{2L}\right)^2} \quad (1)$$

wherein L is the inductance, C is the capacitance and R is the resistance in the circuit. Since the resistance is low, the resonance frequency may be approximated by:

$$f \approx \frac{1}{2\pi}\sqrt{\frac{1}{LC}} \quad (2)$$

The resonance frequency f in hertz, may be measured from graph 450 by measuring the time interval T 470 and calculating:

$$f = \frac{1}{T} \quad (3)$$

By combining equations (2) and (3) we can estimate the inductance L by:

$$L = \frac{T^2}{4C\pi^2} \quad (4)$$

The envelop 480 of trace 450 decays exponentially with damping factor α given by:

$$\alpha = \frac{R}{2L} \quad (5)$$

such that that trace 450 is given approximately by:

$$e^{-\alpha t} \sin(2\pi ft) \quad (6)$$

where t is the time. Thus, the resistance R may be estimated by:

$$R = 2L\alpha \quad (7)$$

Figure 5A:
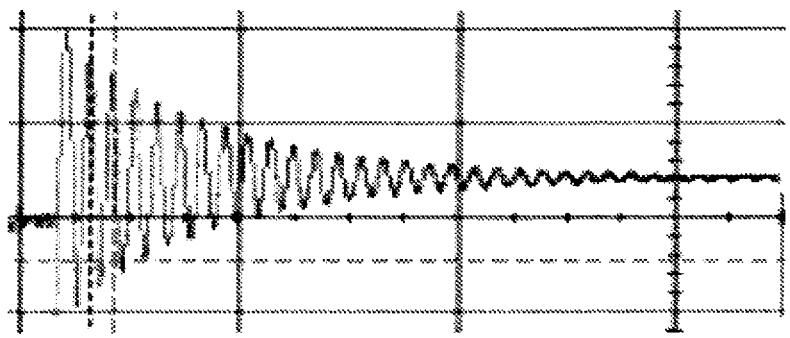
FIG. 5A depicts the voltage measured on the primary coil after pulse excitation where no receiver was placed in proximity to the primary coil.
Figure 5B:
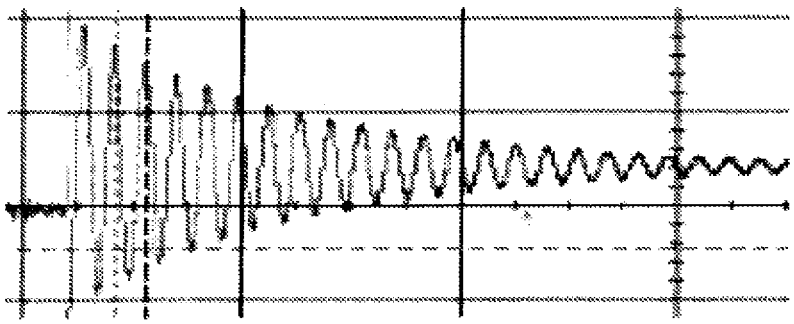
FIG. 5B depicts the voltage measured on the primary coil after pulse excitation where ferromagnetic material was placed in proximity to the primary coil, representing coupling to an unloaded secondary coil.
Figure 5C:
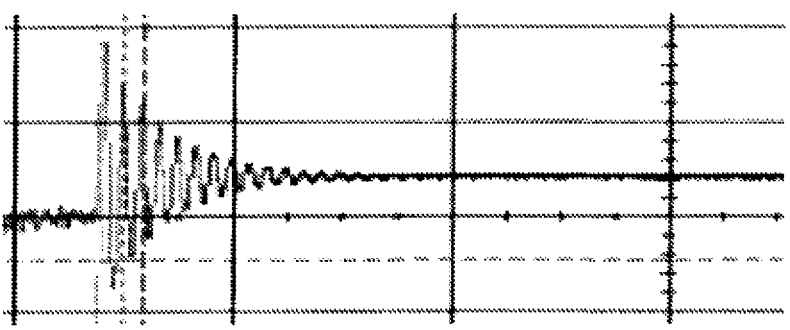
FIG. 5C depicts the voltage measured on a primary coil after pulse excitation where a thin layer of copper was placed in proximity to the primary coil, representing incorrect placement of an object, or placement of foreign object on the transmitter.

FIGS. 5A, 5B and 5C depict voltages measured on a primary coil 220 after pulse excitation in different conditions, wherein:

FIG. 5A depicts the voltage measured on a primary coil 220 after pulse excitation where no receiver was placed in proximity to the primary coil.

FIG. 5B depicts the voltage measured on a primary coil 220 after pulse excitation where ferromagnetic material was placed in proximity to the primary coil, representing coupling to an unloaded secondary coil 260.

FIG. 5C depicts the voltage measured on a primary coil 220 after pulse excitation where a thin layer of copper was placed in proximity to the primary coil, representing incorrect placement of an object, or placement of a foreign object on the transmitter.

From FIG. 5A the natural resonance frequency of the transmitter circuit may be estimated as f~190.1 kilohertz, and a decay to half the amplitude is in ~25 microseconds.

From FIG. 5B we can see that the resonance frequency of the transmitter circuit decreased to f~141.2 kilohertz, and a decay to half the amplitude is in ~35 microseconds.

This is caused primarily by the increase in coil inductance due to coupling with the ferromagnetic material. It should be noted that in actual systems, secondary coil 260 is fitted with a ferromagnetic core to increase the coupling to the primary coil 220, thus ensuring efficient energy transfer. The 26% change in resonance frequency is easy to detect and is in agreement with equation (2), indicating a 1.8 times increase in inductance. Similarly, the decay time increases by ~35% in agreement with the prediction of equation (5) and (6) when the inductance increases. From equation (7) we can estimate that the equivalent resistance due to losses increased by approximately 25%.

From FIG. 5C we can see that the resonance frequency of the transmitter circuit increased to f~244 kilohertz, and decay to half the amplitude is in ~12.5 microseconds.

The two-fold decrease in decay time is an indication of power loss due to Eddy current induced in the conductive foil by the time varying magnetic field produced by the current in the primary coil 220. It should be noted that placing an object comprising conductive material such as metals would cause such power loss and result in decrease in decay time. For example, aluminum foils within a cigarette pack, a metal plate and the likes may be identified thus a foreign object. Similarly, if a device equipped with a receiver 290 is placed on transmitter 110 incorrectly such that secondary coil 260 is not adequately aligned with primary coil 220, some of the energy radiated from primary coil 260 during the testing process discloses.

It should be noted that often the secondary coil 290 comprises a ferromagnetic core to increase the inductive coupling with the primary coil 220. The increase in effective inductance of the primary coil is to a large extant due to the influence of the ferromagnetic core that is now in close proximity to the primary coil. Additionally, the loading state of the secondary coil may influence its effect on the resonance parameters of the primary coil. For example, if the secondary coil 290 is shorted, or resistively loaded, it may contribute to losses (and apparent increase in resistance) in the primary coil 220. This is caused by energy transferred from (and thus lost to) the primary coil, similarly to the effect of placing a conductive foil or a metallic object near the primary coil, as seen in FIG. 5C.

Figure 6A:
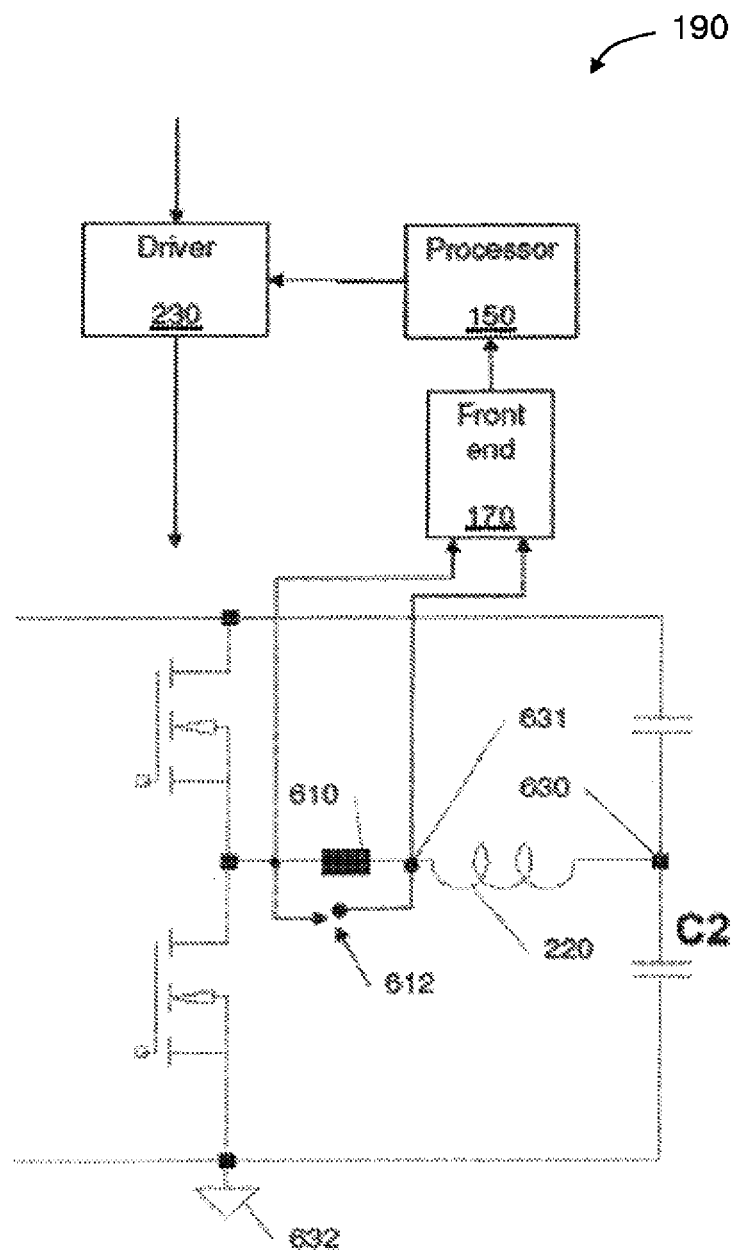
FIG. 6A schematically depicts a block diagram of the main elements of an inductive power transfer system which uses a series resistor during detection of inductive coupling according to an exemplary embodiment of the current invention.

FIG. 6A schematically depicts a block diagram of the main elements of an inductive power transfer system which uses a series resistor during detection of inductive coupling according to an exemplary embodiment of the current invention.

Voltages developed on primary coil 220 may be high during the pulse excitation and during power transmission to the receiver 290. For example, voltages of tens of volts were measured during the experiments disclosed in FIGS. 4 and 5A-C.

In some embodiments front end is protected, for example by AC coupling, signal attenuation, voltage restriction such as Zener Diodes, and the likes.

In other embodiments, front end 170 is disconnected during power transmission, and pulse excitation for the purpose of detection of the inductive coupling is performed at reduced voltage of power supply 240. Reducing the voltage also reduces the power needed for such detection. According to an exemplary embodiment depicted in FIG. 6A, a resistor 610 is placed in series to primary coil 612. The value of resistor 610 is set to be small as not to degrade the resonance properties of the circuit, and to produce detectable signal in response to the current flowing through the coil. An optional bypass switch 612 may be closed during power transmission. Closing bypass switch 612 serves to protect front end 170 and to eliminate power loss in the resistor during power transmission.

It should be noted that other points in the circuit may be used by front end 170 for probing voltages. For example, the voltage on capacitor C2 may be probed by measuring the voltage between its terminal 630 and ground 632. Other points may also be similarly used.

Figure 6B:
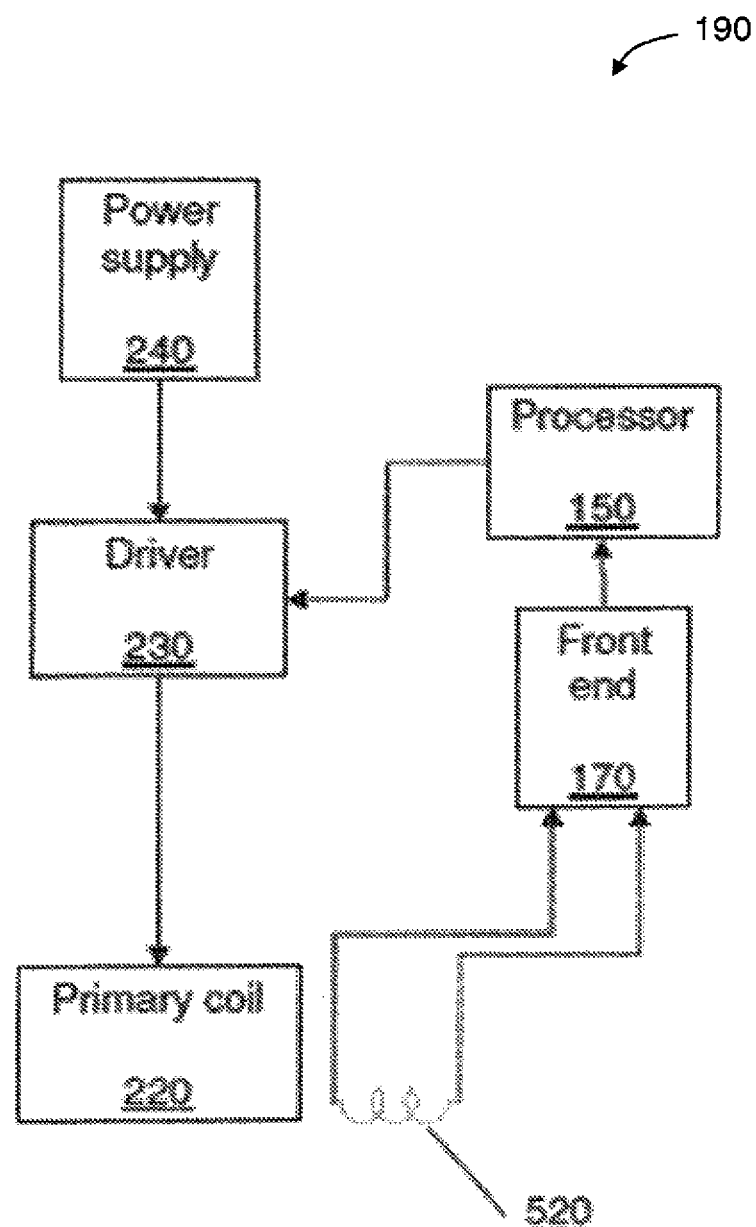
FIG. 6B schematically depicts a block diagram of the main elements of an inductive power transfer system which uses a probing coil 520 for detection of inductive coupling according to an exemplary embodiment of the current invention.

FIG. 6B schematically depicts a block diagram of the main elements of an inductive power transfer system which uses a probing coil 520 for detection of inductive coupling according to an exemplary embodiment of the current invention.

Optionally the probing coil 520 is a small auxiliary coil placed near or over the primary coil 220 such that it picks up some of the electromagnetic radiation from the primary coil. Probing coil 520 is used as a pickup device and the signals on it follow the changes in current at the primary coil 220.

Front end 170 is used for transforming analog signals indicative of the behavior of the resonant circuit to digital signals to be used by processor 150 in order to determine proper inductive coupling between primary coil 220 and secondary coil.

In one example, front end 170 comprises an Analog to Digital Converter (ADC). Since the frequency range of the typical signals is in the tens to hundreds kilohertz range, the sampling rate should be high enough to avoid aliasing. However, if the resonance frequency is to be determined, accuracy (number of bits) may be limited, for example an 8-bit ADC may be used. Front end may further comprise a Digital Signal Processor (DSP), or a processor 150 may be used for analyzing the ADC results.

For calculating the resonance frequency, a limited number of signal cycles may be digitized, thus limiting the amount of data that has to be stored and processed. For example, zero crossing of a sinusoidal signal may be accurately assessed from data fitting and interpolation. By timing at least two and optionally a few zero crossings, the frequency may be accurately estimated. Alternatively, computation-efficient FFT and DFT (Fast Fourier Transform and Digital Fourier Transform) algorithms may be used to determine the resonant frequency, For estimating the decay parameter of the signal, the peaks (or area) of at least two, and optionally a few signal cycles needs to be measured. Preferably, the measured cycles are separated in time such that amplitude difference between them is substantial.

It should be noted, that optionally several types of receivers 290 may be designed and operate with same type of transmitter 110. Each of such receiver types may be associated with a change in the resonance parameters of the primary coil which may be characteristic. Thus, the processor 150 may compare the assessed parameters with a list of allowed parameters. It should also be noted that each set of parameters in the list may be associated with (optionally different) acceptance range. Thus, processor 150 may need only to establish one of the following:

No change detected in the resonance parameters of the primary coil. In this case—continue monitoring.

A change was detected in the resonance parameters of the primary coil, and the new parameters match coupling to a valid receiver. In this case—start power transmission.

A change was detected in the resonance parameters of the primary coil, and the new parameters do not match coupling to a valid receiver. In this case—Optionally issue warning to user, and continue monitoring.

Since the number of valid resonance frequencies is limited to the resonance frequency of uncoupled primary coil plus the frequencies associated with each of valid receiver type, a set of tuned filtered may be used in order to identify the resonance parameters of the primary filter.

For example, a digital filter may be used. Such filters are known in the art and may be found for example in http://en.wikipedia.org/wiki/Digital_filter and in the Numerical Recipes series of books on algorithms and numerical analysis by William H. et al.

Alternatively, a set of analog filters may be used. For example a set of RLC circuits, each tuned to one specific resonance frequency, or a single circuit, tuned each time to a different frequency, for example by means of a variable capacitor, or a set of capacitors.

Other analog tuned circuits may be used such as Surface Acoustic Wave (SAW) devices.

An advantage of using tuned filters is that their output has reduced noise, and thus more accurate measurements may be performed. For example, filtered signals may be amplified without risk of overloading, and may be used for more accurate determination of the decay envelope of the signal.

Alternatively a lock-in amplifier (also known as a phase-sensitive detector or coherent detection) may be used, tuned to the specific expected frequencies, or with swept frequencies.

In some embodiments of the invention, front end 170 comprises at least one analog signal processing unit or function that reduces the computation requirement. For example, a zero crossing detector may be used to produce digital signal indicative of the times in which the detected signal crosses the zero level. By measuring the time interval between zero crossings, the resonance frequency may be determined. A person skilled in the art of electronics may design other means of analog signal processing such as Schmitt trigger and Time-to-voltage converter, all of which may be obtained commercially.

Similarly, decay parameter of the signal may be assisted by analog signal processing such as a peak detector which allows using a slow ADC, and one digitizing sample for obtaining the peak voltage of a signal cycle. Alternatively, the signal may be rectified and low-pass filtered to create a monotonic smooth representation of the envelope of the signal.

In an exemplary embodiment, two different threshold levels are used in an analog comparator to determine the times these levels were crossed. The damping parameter may be determined by measuring the time difference between the last time the high threshold level was crossed and the last time the lower threshold level was crossed.

It should be noted that when two parameters of the inductive coupling are measured (frequency and decay) the identification of the proper alignment of the secondary coil 260 is reliably determined Thus, the probability of turning on power transmission when a foreign object is placed on the transmitter is reduced. For example, a magnetic switch used as sensor 160 may be activated by an object having magnetic properties such as a refrigerator magnet which may be heated, melt or case damage if exposed to electromagnetic radiation emitted from the transmitter.

The current invention may provide cost saving in manufacturing the transmitter 110 as it saves the necessity for providing sensor 160. It should be noted that the most or all the components needed for the operation of invention may already exist in the transmitter and are used for controlling the transmitter during power transmission.

Additionally, the current invention may provide cost saving in designing and manufacturing the receiver 290. For example, already designed and used receivers may be used without modification by transmitters according to the current invention.

Additionally, the current invention requires no transmission of signal from the receiver in order for it to be detected. This saves the necessity for providing any active or passive means in receiver 290 in order to be detected by sensor 160. Additionally, placement of receiver 290 may be reliably detected, and power transmission may commence even if batteries in receiver 290 are completely depleted such that it cannot establish data communication with transmitter 110 until at least some power was received by receiver 290.

In FIG. 4, a wide square excitation pulse was used. It should be noted that optionally a narrow pulse, having a width comparable or even narrower that one cycle of the resonance frequency may be used. Waveforms other than rectangular pulse may be used for excitation.

In another embodiment of the current invention, excitation is in a form of alternating signal, and the amplitude and optionally the amplitude and/or phase response of the resonance circuit is measured in order to determine the resonance frequency and optionally the decay parameter.

For example, excitation may be in the form of weak AC (square, sinusoidal, or other) signal at various frequencies. In an exemplary embodiment, the excitation is frequency-swept over the range of frequencies including the resonance frequencies of coupled and uncoupled primary coil, while the response is measured. The peak response indicates the actual resonance frequency. Damping factor α may be estimated from the value of the maximum response as well as from the frequency width of the peak.

In another embodiment, several alignment coils it may be used to quantify the alignment of secondary coil 260 relative to the primary coil 220. For example three or more alignment coils may be used for providing information on the direction of misalignment.

Figure 7:
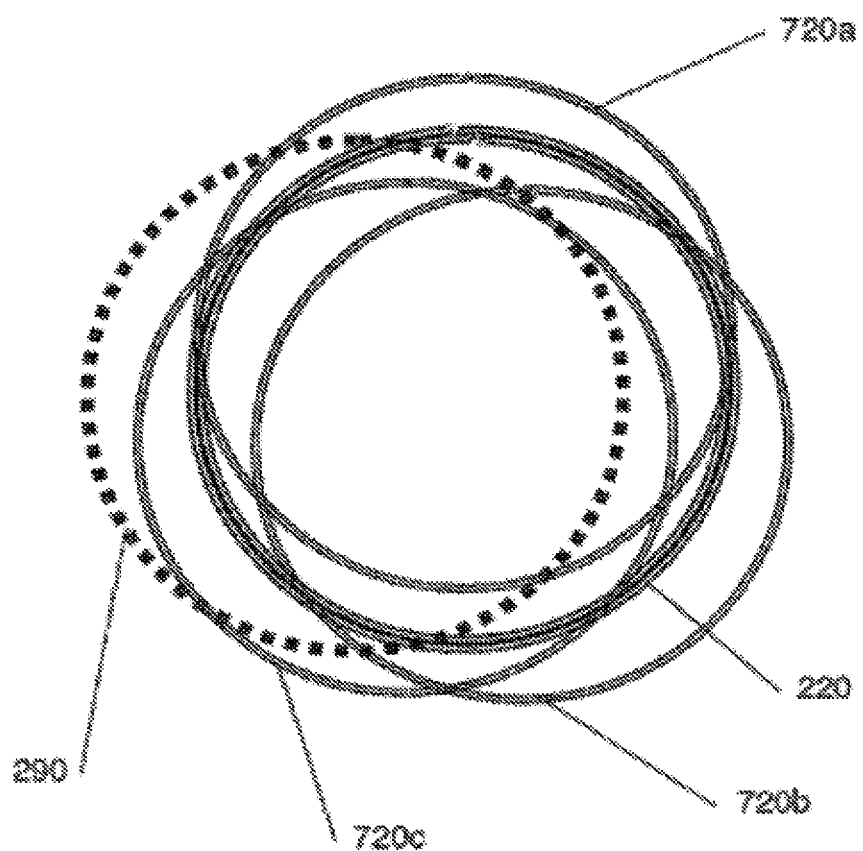
FIG. 7 schematically depicts a spatial positioning of a primary coil and three alignment coils according to an exemplary embodiment of the current invention.

FIG. 7 schematically depicts a spatial positioning of a primary coil 220 and three alignment coils 720a, 720b and 720c according to an exemplary embodiment of the current invention.

When a secondary coil 290 is misaligned with primary coil 220, its coupling to alignment coils 720a, 720b and 720c is unequal. by comparing the coupling of secondary coil 290 to each of the three alignment coils, the direction and possibly the amount of misalignment may be determined.

Figure 8:
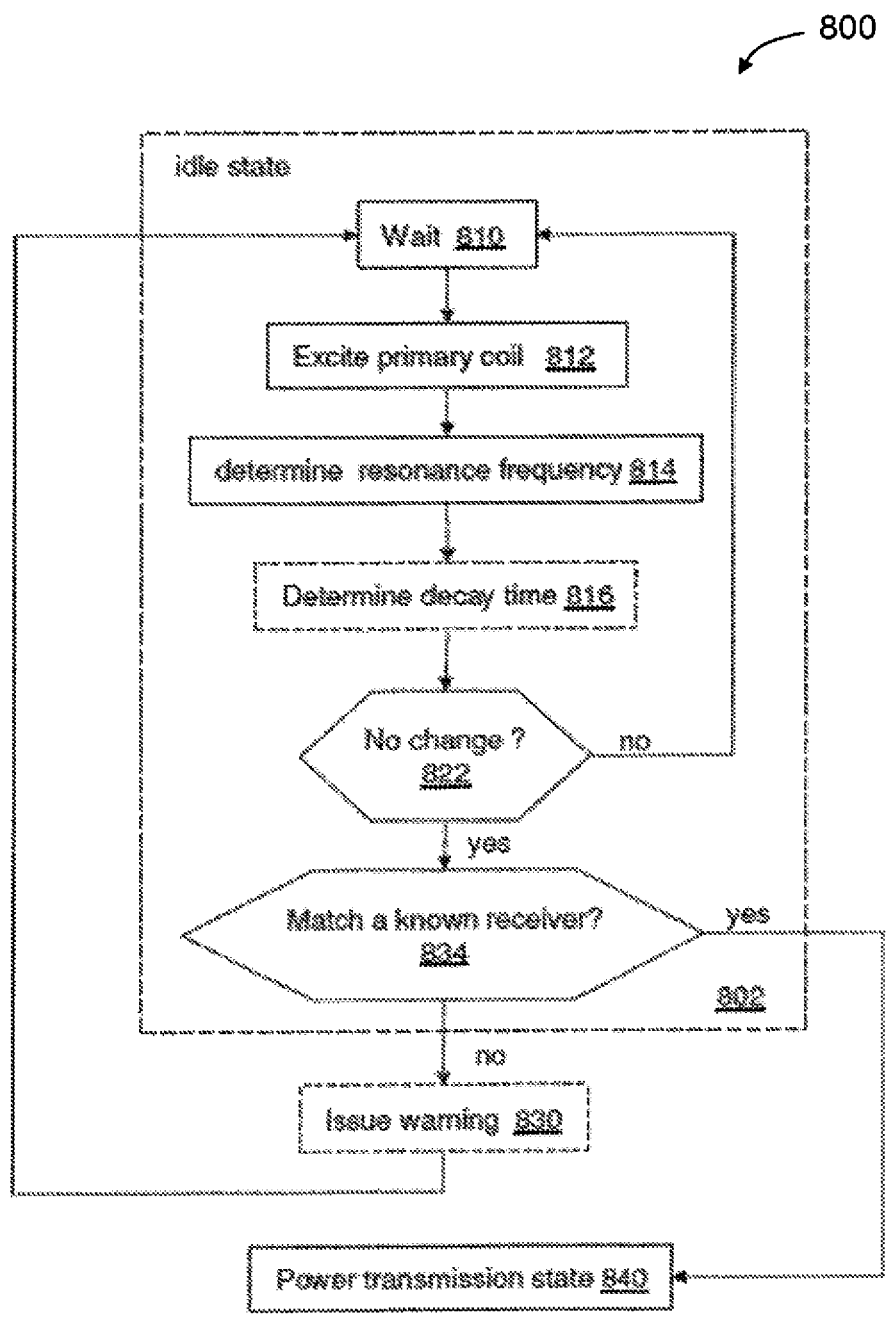
FIG. 8 schematically depicts a method for triggering power transmission from the transmitter to the receiver according to an exemplary embodiment of the current invention.

FIG. 8 schematically depicts a method 800 for triggering power transmission from a transmitter 110 to receiver 290 according to an exemplary embodiment of the current invention.

Transmitter 110 enters an idle state 802 when it is turned on, or after power transmission terminates. In this state, most of the time the transmitter 110 is in "wait" mode 810, where power consumption may be at minimum required for operating an internal clock. After a predefined duration, (for example every 1 second, however, shorter or longer may be used), primary coil 220 is excited 812. Resonance frequency is determined 814, and optionally, the decay time is determined 816. In step 822, the effective inductance, and optionally the effective resistance in the primary coil circuit are assessed and compared with the predicted, measured or otherwise known parameters indicative of a primary coil free of influences external to the transmitter 110. If no change is observed in the assessed parameters, the transmitter stays in idle state 802 and wait step 810 is repeated.

If change or changes are observed in the assessed parameters, the parameters are compared 834 with the predicted, measured or otherwise known parameters indicative of a correct placement and alignment of a receiver 290. If the assessed parameters are matched with parameters indicative of a well places receiver 290 which is designed to be coupled with transmitter 110 power transmission starts 840. Optionally, the transmission frequency may be selected according to the determined resonance frequency. Where appropriate, the transmission frequency may be selected to be approximately equal to the resonant frequency. Alternatively a transmission frequency above or below the resonant frequency of the system may be selected, as described hereinbelow.

It should be noted, that optionally several types of receivers 290 may be designed and operate with same type of transmitter 110. Thus, processor 150 may compare the assessed parameters with a list of allowed parameters. It also should be noted that each set of parameters in the list may be associated with (optionally different) acceptance range. Additionally, processor 150 may identify the type of receiver used by matching the assessed parameters to the parameters in the list and adjust the parameters used for power transmission 840. Additionally, transmitter 110 may attempt to establish communication with the receiver 290, optionally based on the identification of the type of receiver 290.

Figure 9:
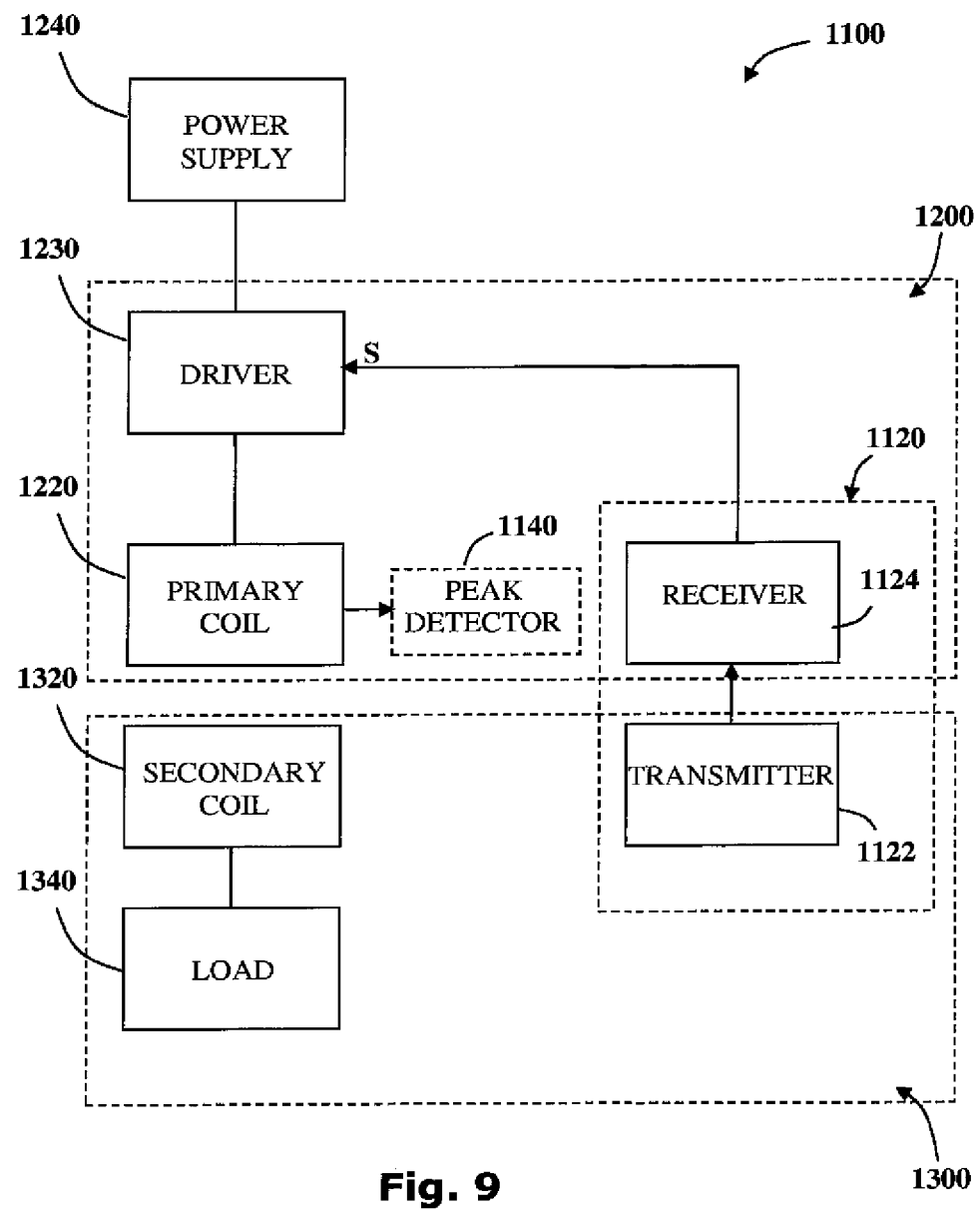
FIG. 9 is a block diagram showing the main elements of an inductive power transfer system with a feedback signal path according to embodiments of the present invention.

Reference is now made to FIG. 9 showing a block diagram of the main elements of an inductive power transfer system 1100 adapted to transmit power at a non-resonant frequency according to another embodiment of the invention. The inductive power transfer system 1100 consists of an inductive power outlet 1200 configured to provide power to a remote secondary unit 1300. The inductive power outlet 1200 includes a primary inductive coil 1220 wired to a power source 1240 via a driver 1230. The driver 1230 is configured to provide an oscillating driving voltage to the primary inductive coil 1220.

The secondary unit 1300 includes a secondary inductive coil 1320, wired to an electric load 1340, which is inductively coupled to the primary inductive coil 1220. The electric load 1340 draws power from the power source 1240. A communication channel 1120 may be provided between a transmitter 1122 associated with the secondary unit 1300 and a receiver 1124 associated with the inductive power outlet 1200. The communication channel 1120 may provide feedback signals S and the like to the driver 1230.

In some embodiments, a voltage peak detector 1140 is provided to detect large increases in the transmission voltage. As will be descried below the peak detector 1140 may be used to detect irregularities such as the removal of the secondary unit 1200, the introduction of power drains, short circuits or the like.

Figure 10:
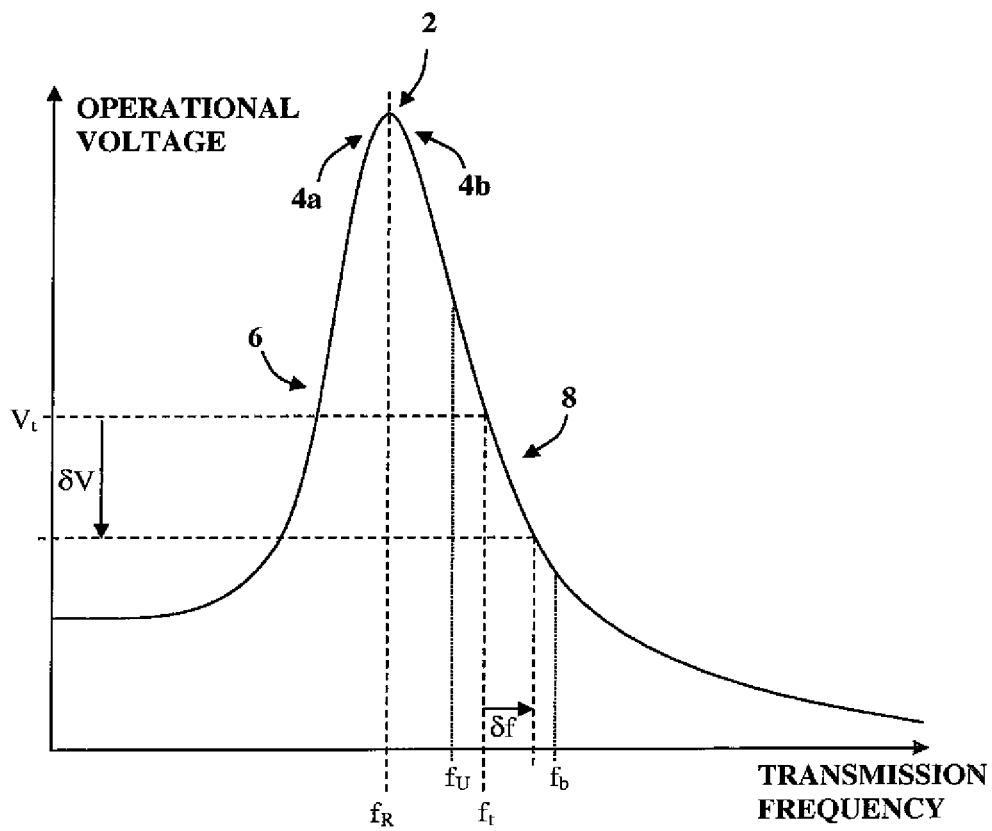
FIG. 10 is a graph showing how the amplitude of operational voltage of an inductive power transfer system varies with transmission frequency.

FIG. 10 is a graph showing how the amplitude of the operational voltage of an inductive power transfer system varies according to the transmission frequency. It is noted that the voltage is at its highest when the transmission frequency is equal to the resonant frequency $f_R$ of the system, this maximum amplitude is known as the resonance peak 2. It is further noted that the slope of the graph is steepest in the regions 4a, 4b to either side of the resonance peak 2. Thus in inductive transfer systems, which operate at or around resonance, a small variation in frequency results in a large change in induced voltage. Similarly, a small change in the resonant frequency of the system results in a large change in the induced voltage. For this reason prior art resonant inductive transfer systems are typically very sensitive to small fluctuations in environmental conditions or variations in alignment between the induction coils.

It is a particular feature of embodiments of the current invention that the driver 1230 (FIG. 9) is configured and operable to transmit a driving voltage which oscillates at a transmission frequency which is substantially different from the resonant frequency of the inductive couple. Preferably the transmission frequency is selected to lie within one of the near-linear regions 6, 8 where the slope of the frequency-amplitude graph is less steep.

Figure 11:
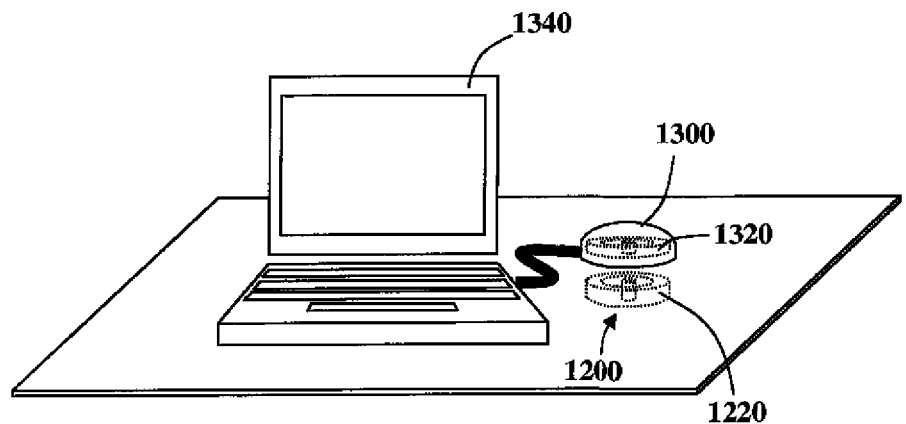
FIG. 11 is a schematic diagram representing a laptop computer drawing power from an inductive power outlet.

One advantage of this embodiment of the present invention may be demonstrated with reference now to FIG. 11. A schematic diagram is shown representing a laptop computer 1340 drawing power from an inductive power outlet 1200 via a secondary power receiving unit 1300. The power receiving unit 1300 includes a secondary inductive coil 1320 which is aligned to a primary inductive coil 1220 in the inductive power outlet 1200. Any lateral displacement of the secondary power receiving unit 1300 changes the alignment between the secondary inductive coil 1320 to the primary inductive coil 1220. As a result of the changing alignment, the combined inductance of the coil pair changes which in turn changes the resonant frequency of the system.

If the inductive power outlet 1200 transmits power at the resonant frequency of the system, even a small lateral movement would reduce significantly the amplitude of the induced voltage. In contradistinction to the prior art, in embodiments of the present invention the inductive power outlet 1200 transmits power at a frequency in one of the regions 6, 8 to either side of the resonance peak 2 (FIG. 10) where the slope of the resonance graph is much shallower. Consequently, the system has a much larger tolerance of variations such as lateral movement.

A further feature of embodiments of inductive power outlets transmitting at frequencies above the natural resonant frequency of the system is that if the resonant frequency of the system increases for some reasons, then the transmission voltage increases sharply. In preferred embodiments, a peak detector 1140 (FIG. 9) is be provided to monitor the transmission voltage of the power outlet 1200 and is configured to detect large increases in the transmission voltage indicating an increase in resonant frequency.

Referring again to the resonant formula for inductive systems, $$f_R = \frac{1}{2\pi\sqrt{LC}},$$

it is noted that any decrease in either the inductance L or the capacitance C of the system increases the resonant frequency and may be detected by the peak detector 1140. Similarly, from the formula for damped resonance (1) above, as the resistance increases, the effective resonant frequency increases.

As an example of the use of a peak detector 1140, reference is again made to FIG. 11. It will be appreciated that in a desktop environment, conductive bodies such as a paper clip, metal rule, the metal casing a stapler, a hole-punch or any metallic objects may be introduced between the inductive power outlet 1200 and the secondary power receiving unit 1300. The oscillating magnetic field produced by the primary coil 1220 would then produce eddy currents in the conductive body heating it and thereby draining power from the primary coil 1220. Such a power drain may be wasteful and/or dangerous. Power drains such as described above generally reduce the inductance L of the system thereby increasing its resonant frequency.

The inductance L of the system may also be reduced by the removal of the secondary coil 1220, the creation of a short circuit or the like. A peak detector 1140, wired to the inductive power outlet, may detect any of these scenarios as a large increase in transmission voltage. Where required, the power transfer system may be further configured to shut down, issue a warning or otherwise protect the user and the system in the event that the peak detector 1140 detects such an increase in transmission voltage.

Figure 12:
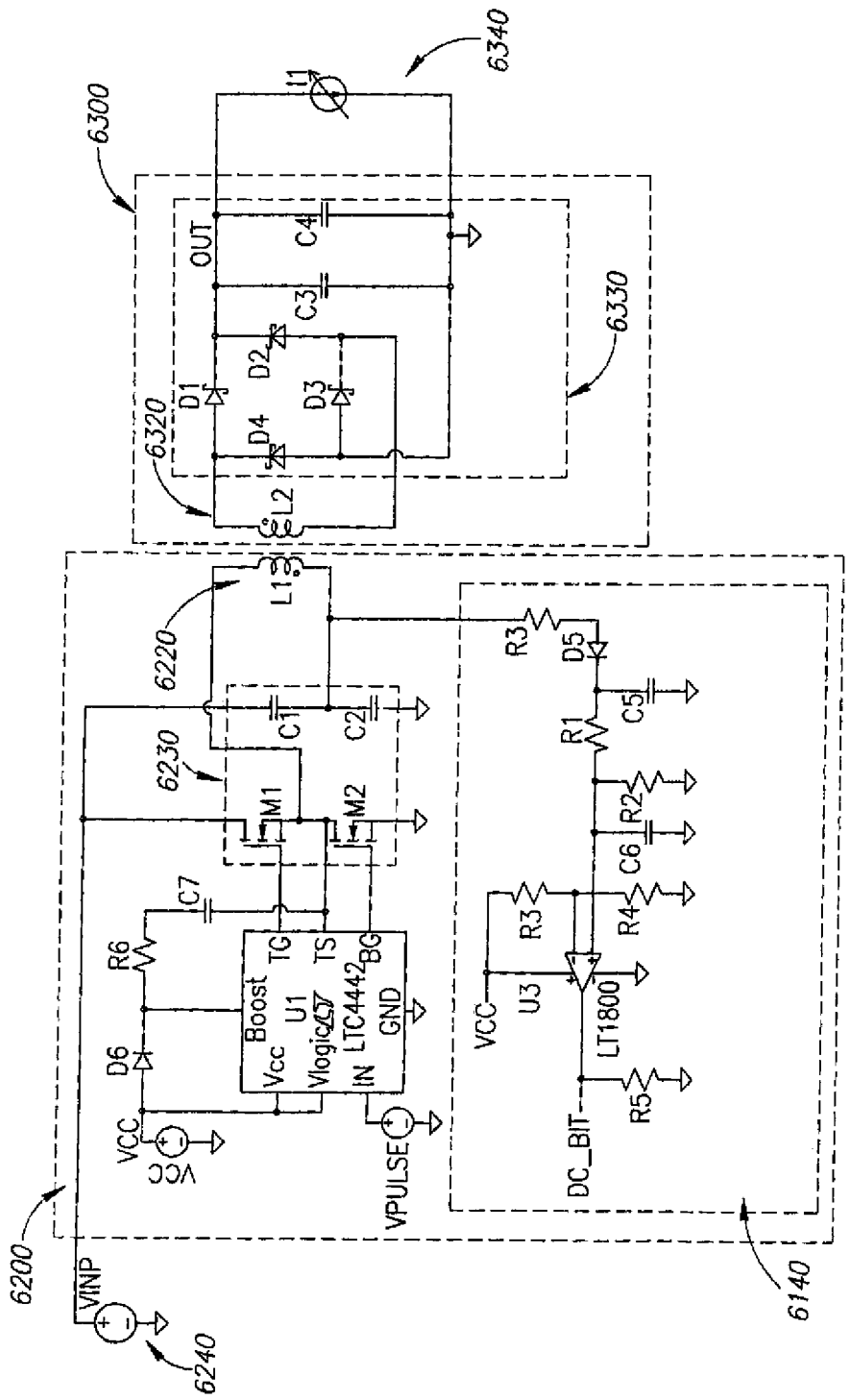
FIG. 12 is a circuit diagram of an inductive power transfer system according to another embodiment of the invention including a peak detector for detecting large increases in transmission voltage.

FIG. 12 is a circuit diagram of an inductive power outlet 6200 and secondary unit 6300. The secondary unit 6300 comprises a secondary coil 6320 wired to an electric load 6340 via a rectifier 6330.

The inductive power outlet 6200 comprises a primary coil 6220 driven by a half-bridge converter 6230 connected to a power source 6240. The half-bridge converter 6230 is configured to drive the primary coil 6220 at a frequency higher than the resonant frequency of the system and a peak detector 6140 is configured to detect increases in the transmission voltage.

Although only a half-bridge converter is represented in FIG. 12, it is noted that other possible driving circuits include: a DC-to-DC converter, an AC-to-DC converter, an AC-to-AC converter, a flyback transformer, a full-bridge converter, a flyback converter or a forward converter for example.

Another advantage of non-resonant transmission is that the transmission frequency may be used to regulate power transfer. Prior art inductive power transfer systems typically regulate power transfer by altering the duty cycle of the transmission voltage. Unlike prior art systems, because embodiments of the present invention transmit at a frequency not equal to the resonant frequency of the system, the driver 1230 may be configured to regulate power transfer by adjusting the transmission frequency.

The regulation is illustrated with reference to FIG. 10. In embodiments of the invention, the frequency of transmission may be selected to be in the approximately linear region 8 of the curve between a lower frequency value of $f_L$ and an upper frequency value of $f_U$. A transmission frequency $f_t$, higher than the resonant frequency $f_R$ of the system, produces an induced voltage of $V_t$. The induced voltage can be increased by reducing the transmission frequency so that it is closer to the resonant frequency $f_R$. conversely, the induced voltage may be reduced by increasing the transmission frequency so that it is further from the resonant frequency $f_R$. For example, an adjustment of transmission frequency by $\delta f$ produces a change in induced voltage of $\delta V$.

In some embodiments, a communication channel 1120 (FIG. 9) is provided between the secondary unit 1300 and the inductive power outlet 1200 to communicate the required operating parameters. In embodiments of the invention operating parameters the communication channel 1120 may be used to indicate the transmission frequency required by the electric load 1340 to the driver 1230.

The communication channel 1120 may further provide a feedback signal during power transmission. The feedback transmission may communicate required or monitored operating parameters of the electric load 1240 such as:

required operating voltage, current, temperature or power for the electric load 1240, the measured voltage, current, temperature or power supplied to the electric load 1240 during operation, the measured voltage, current, temperature or power received by the electric load 1240 during operation and the like.

In some embodiments, a microcontroller in the driver 1230 may use such feedback parameters to calculate the required transmission frequency and to adjust the driver accordingly. Alternatively, simple feedback signals may be provided indicating whether more or less power is required.

Figure 13:
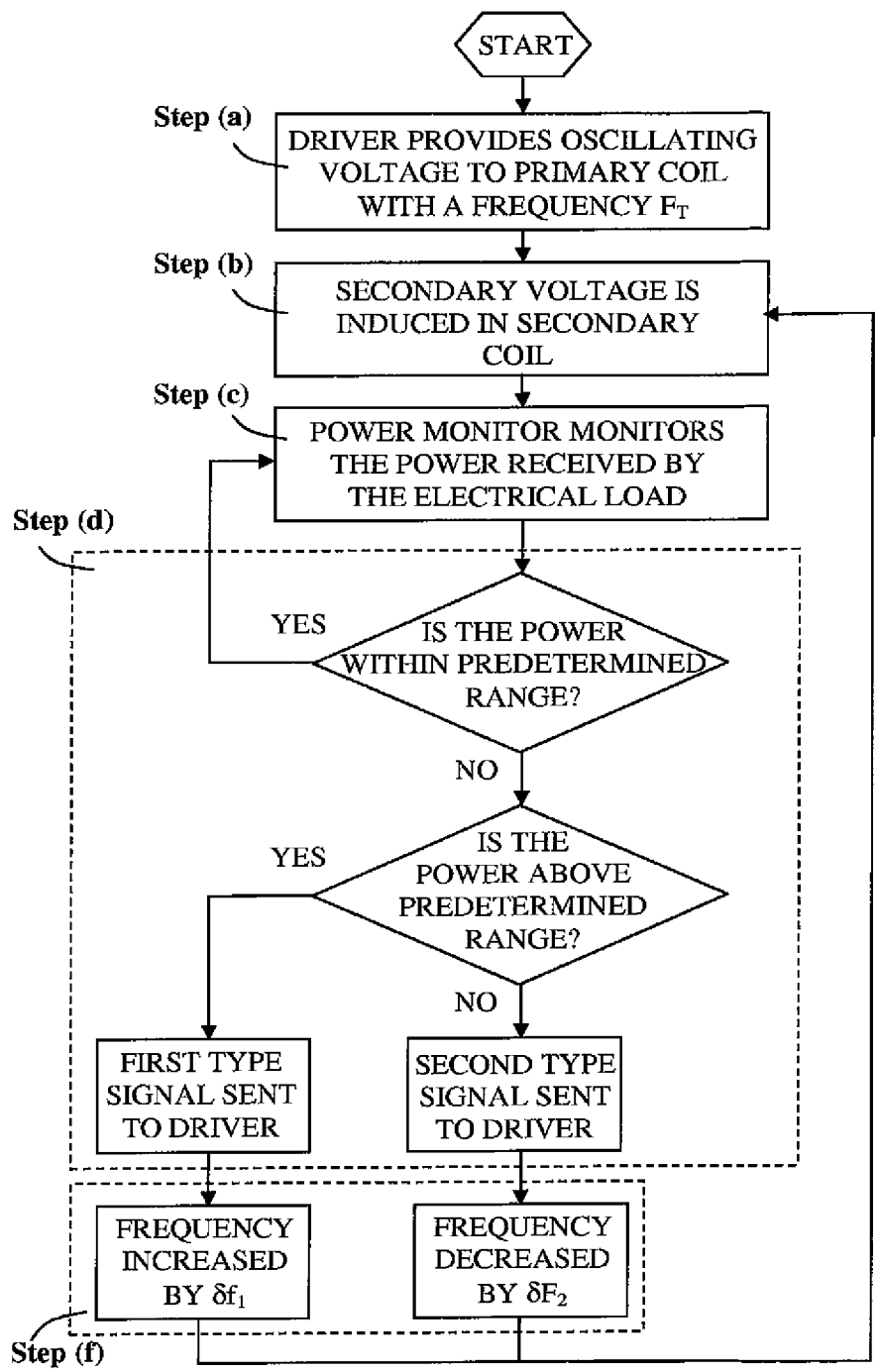
FIG. 13 is a flowchart showing a method for regulating power transfer by varying the power transmission frequency in an inductive power transfer system according to a further embodiment of the invention.

One example of a power regulation method using simple feedback signals is shown in the flowchart of FIG. 13. The method involves the following steps:

Step (a)—The driver 1230 provides an oscillating voltage at a transmission frequency $f_t$ which is higher than the resonant frequency $f_R$ of the system.

Step (b)—A secondary voltage is induced in the secondary coil 1320.

Step (c)—A power monitor in the secondary unit 1300, monitors the power received by the electric load 1340.

Step (d)—If the power received by the electric load 1340 lies within a predetermined range then no action is taken. If the power received by the electric load 1340 is below the predetermined range, then a feedback signal of a first type $S_a$ is sent to the driver. If the power received by the electric load 1340 is above the predetermined range, then a feedback signal of a second type $S_b$ is sent to the driver.

Step (e)—A feedback signal is received by the driver 1230.

Step (f)—If the received feedback signal is of the first type $S_a$, then the transmission frequency is increased by an incremental value $+\delta f_1$. If the received feedback signal is of the second type $S_b$, then the transmission frequency is decreased by an incremental value $-\delta f_2$.

It is noted that by using the power regulation method described above, when the power received by the load is too high, a series of feedback signals of the first type $S_a$ will be transmitted until the power is reduced into the acceptable range. Likewise when the power received by the load is too low, a series of feedback signals of the second type $S_b$ will be transmitted until the power is increased into the acceptable range. It is noted that the positive incremental value $\delta f_1$ may be greater than, less than or equal to the negative incremental value $\delta f_2$.

Alternatively, other power regulation methods using frequency adjustment may be used. For example, the operating parameters of the electric load may be monitored and their values may be transmitted to the power outlet via the communications channel 1120. A processor in the power outlet may then calculate the required transmission frequency directly.

The method described hereinabove, refers to a non-resonant transmission frequency lying within the linear region 8 (FIG. 10), higher than the resonant peak 2. It will be appreciated however that in alternative embodiments frequency-controlled power regulation may be achieved when the transmission frequency lies in the lower linear region of the resonance curve. Nevertheless, for certain embodiments, the selection of transmission frequencies in the higher linear 8 may be preferred, particularly where peak detection, as described above, is required.

Referring back to FIG. 9, various transmitters 1122 and receivers 1124 may be used for the communication channel 1120. Where, as is often the case for inductive systems, the primary and secondary coils 1220, 1320 are galvanically isolated optocouplers, for example, may be used. A light emitting diode serves as a transmitter and sends encoded optical signals over short distances to a photo-transistor which serves as a receiver. However, optocouplers typically need to be aligned such that there is a line-of-sight between transmitter and receiver. In systems where alignment between the transmitter and receiver may be difficult to achieve, optocoupling may be inappropriate and alternative systems may be preferred such as ultrasonic signals transmitted by piezoelectric elements or radio signals such as Bluetooth, Wi-Fi and the like. Alternatively the primary and secondary coils 1220, 1320 may themselves serve as the transmitter 1122 and receiver 1124.

In certain embodiments, an optical transmitter, such as a light emitting diode (LED) for example, is incorporated within the secondary unit 1300 and is configured and operable to transmit electromagnetic radiation of a type and intensity capable of penetrating the casings of both the secondary unit 1300, and the power outlet 1200. An optical receiver, such as a photodiode, a phototransistor, a light dependent resistors of the like, is incorporated within the power outlet 1200 for receiving the electromagnetic radiation.

Figure 14:
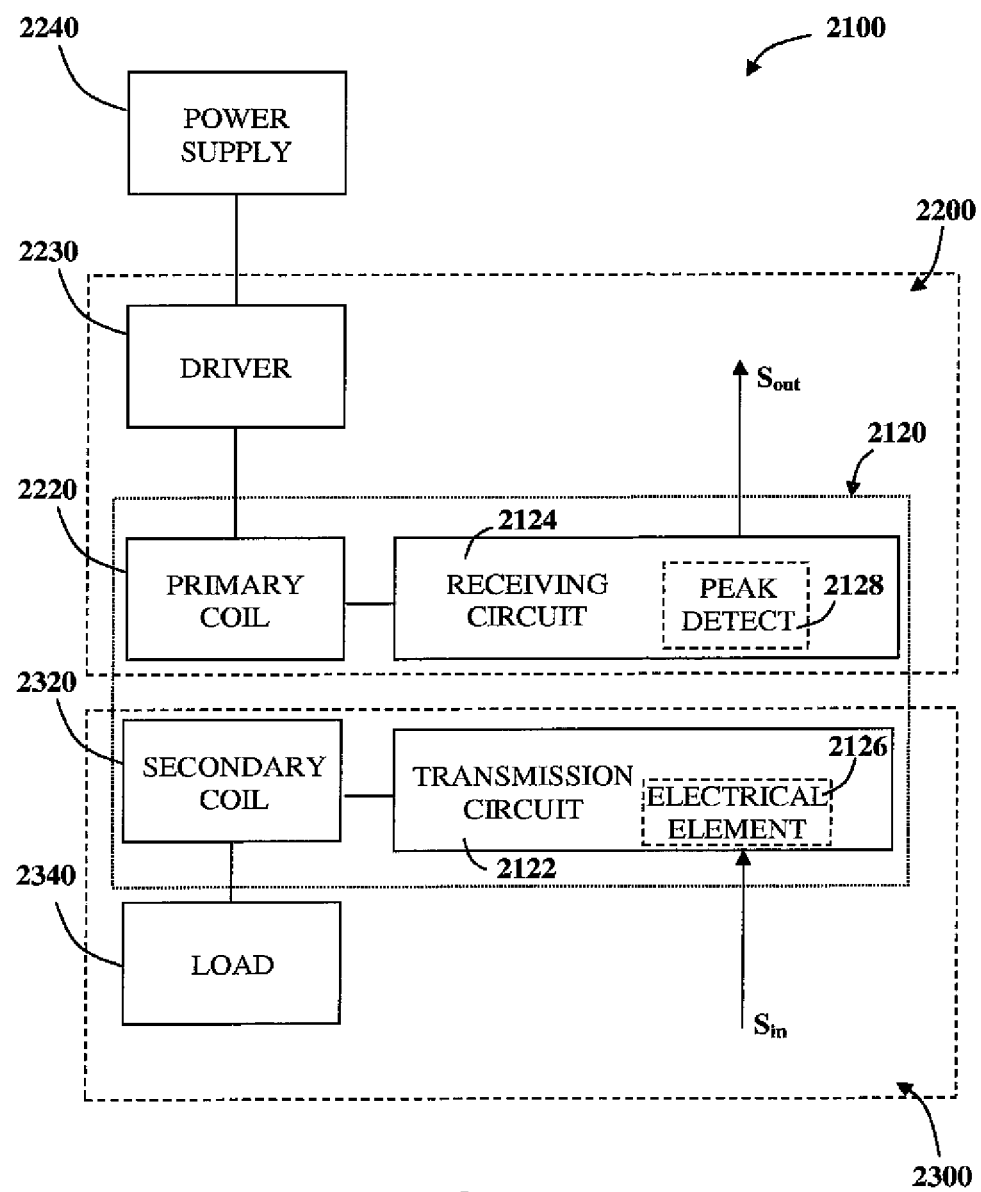
FIG. 14 is a block diagram showing the main elements of an inductive power transfer system with an inductive feedback channel according to still another embodiment of the present invention.

Reference to the block diagram of FIG. 14, it is a particular feature of certain embodiments of the invention that an inductive communications channel 2120 is incorporated into the inductive power transfer system 2100 for transferring signals between a inductive power outlet 2200 and a remote secondary unit 2300. The communication channel 2120 is configured to produce an output signal $S_{out}$ in the power outlet 2200 when an input signal $S_{in}$ is provided by the secondary unit 2300 without interrupting the inductive power transfer from the outlet 2200 to the secondary unit 2300.

The inductive power outlet 2200 includes a primary inductive coil 2220 wired to a power source 2240 via a driver 2230. The driver 2230 is configured to provide an oscillating driving voltage to the primary inductive coil 2220, typically at a voltage transmission frequency $f_t$ which is higher than the resonant frequency $f_R$ of the system.

The secondary unit 2300 includes a secondary inductive coil 2320, wired to an electric load 2340, which is inductively coupled to the primary inductive coil 2220. The electric load 2340 draws power from the power source 2240. Where the electric load 2340 requires a direct current supply, for example a charging device for an electrochemical cell or the like, a rectifier 2330 may be provided to rectify the alternating current signal induced in the secondary coil 2320.

An inductive communication channel 2120 is provided for transferring signals from the secondary inductive coil 2320 to the primary inductive coil 2220 concurrently with uninterrupted inductive power transfer from the primary inductive coil 2220 to the secondary inductive coil 2320. The communication channel 2120 may provide feedback signals to the driver 2230.

The inductive communication channel 2120 includes a transmission circuit 2122 and a receiving circuit 2124. The transmission circuit 2122 is wired to the secondary coil 2320, optionally via a rectifier 2330, and the receiving circuit 2124 is wired to the primary coil 2220.

The signal transmission circuit 2122 includes at least one electrical element 2126, selected such that when it is connected to the secondary coil 2320, the resonant frequency $f_R$ of the system increases. The transmission circuit 2122 is configured to selectively connect the electrical element 2126 to the secondary coil 2320. As noted above, any decrease in either the inductance L or the capacitance C increases the resonant frequency of the system. Optionally, the electrical element 2126 may be have a low resistance for example, with a resistance say under 50 ohms and preferably about 1 ohm.

Typically, the signal receiving circuit 2124 includes a voltage peak detector 2128 configured to detect large increases in the transmission voltage. In systems where the voltage transmission frequency $f_t$ is higher than the resonant frequency $f_R$ of the system, such large increases in transmission voltage may be caused by an increase in the resonant frequency $f_R$ thereby indicating that the electrical element 2126 has been connected to the secondary coil 2320. Thus the transmission circuit 2122 may be used to send a signal pulse to the receiving circuit 2124 and a coded signal may be constructed from such pulses.

According to some embodiments, the transmission circuit 2122 may also include a modulator (not shown) for modulating a bit-rate signal with the input signal $S_{in}$. The electrical element 2126 may then be connected to the secondary inductive coil 2320 according to the modulated signal. The receiving circuit 2124 may include a demodulator (not shown) for demodulating the modulated signal. For example the voltage peak detector 2128 may be connected to a correlator for cross-correlating the amplitude of the primary voltage with the bit-rate signal thereby producing the output signal $S_{out}$.

In other embodiments, a plurality of electrical elements 2126 may be provided which may be selectively connected to induce a plurality of voltage peaks of varying sizes in the amplitude of the primary voltage. The size of the voltage peak detected by the peak detector 2128 may be used to transfer multiple signals.

Figure 15A:
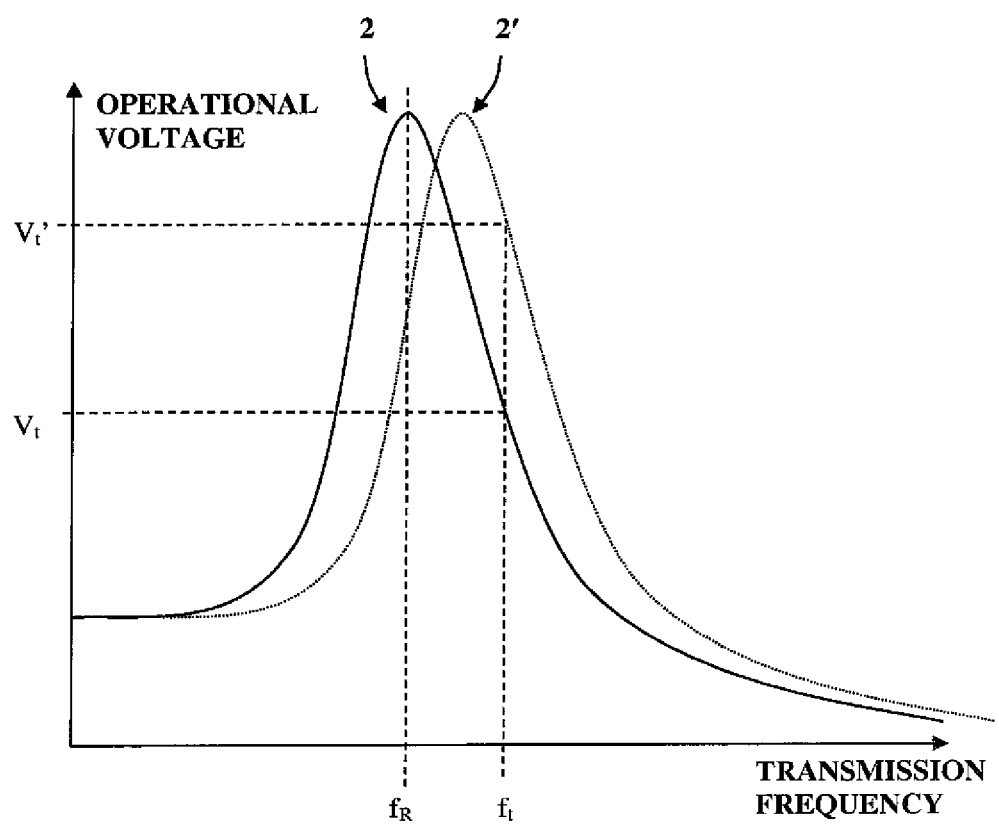
FIG. 15A is a graph showing how the variation of operational voltage with transmission frequency is affected by changes in resonant frequency of the system.

FIG. 15A is a graph showing how the amplitude of the operational voltage varies according to the transmission frequency. It is noted that the voltage is at its highest when the transmission frequency is equal to the resonant frequency $f_R$ of the system, this maximum amplitude is known as the resonance peak 2. If the resonant frequency $f_R$ of the system increases, a new resonance peak 2' is produced.

Figure 15B:
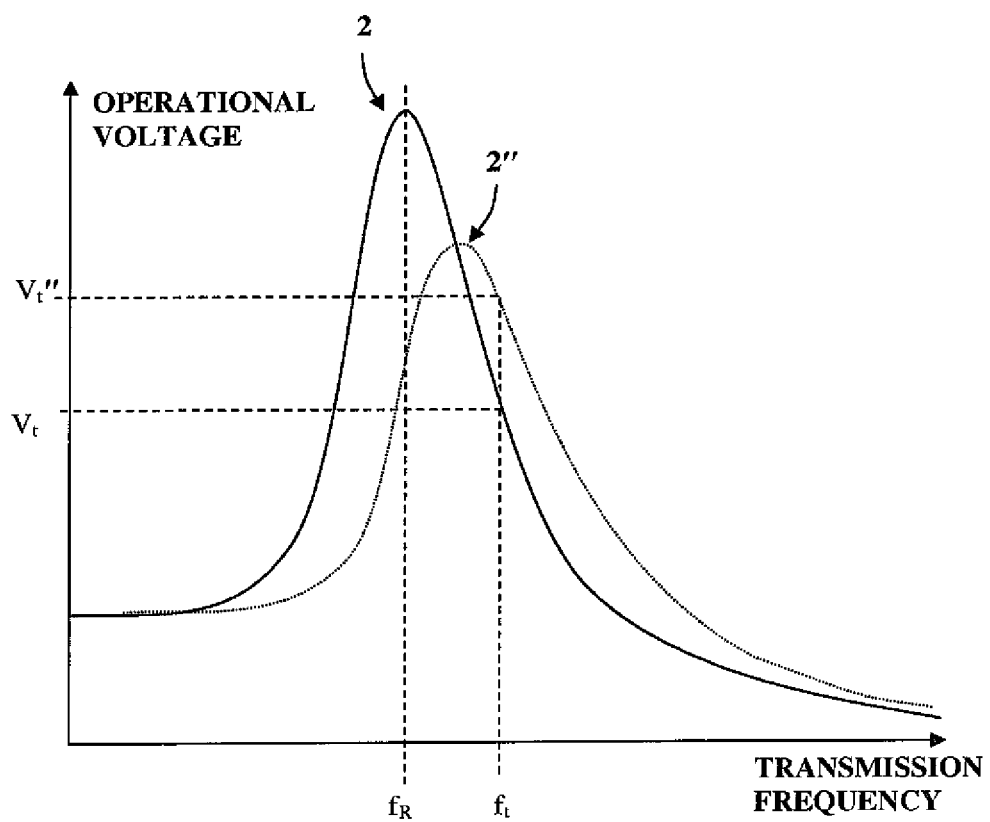
FIG. 15B is a graph showing how the variation of operational voltage with transmission frequency is affected by changes in resonant frequency of the system as a result of damping.

FIG. 15B is a graph showing how the amplitude of the operational voltage varies according to the transmission frequency for damped system. It is noted that in damped systems, for example where a resistor is introduced into the circuit, the resonance curve is shifted and a new effective resonance peak 2" is produced.

Accordingly, where an inductive power transfer system 2100 may be configured to operate at a given transmission frequency $f_t$ higher than the resonant frequency $f_R$ of the system. The normal operating voltage $V_t$ of such a system may be monitored by the voltage peak detector 2128. When the electric element 2126 is connected to the secondary inductive coil 2320 the resonant frequency of the system increases, either due to a decrease in inductance, a decrease in capacitance or through damping effects of an increase in resistance. Therefore, the operating voltage increases to a higher value $V_t'$, $V_t''$. This increase is detected by the voltage peak detector 2128.

It is noted that in contradistinction to prior art inductive signal transfer systems such as described in U.S. Pat. No. 5,455,466 to Terry J. Parks and David S. Register, the present invention enables data signals to be transferred from the secondary coil 2320 to the primary coil 2220 concurrently with inductive transfer of power from the primary coil 2220 to the secondary coil 2320. Consequently, the signal transfer system may be used to provide feedback signals for real time power regulation.

Figure 16A:
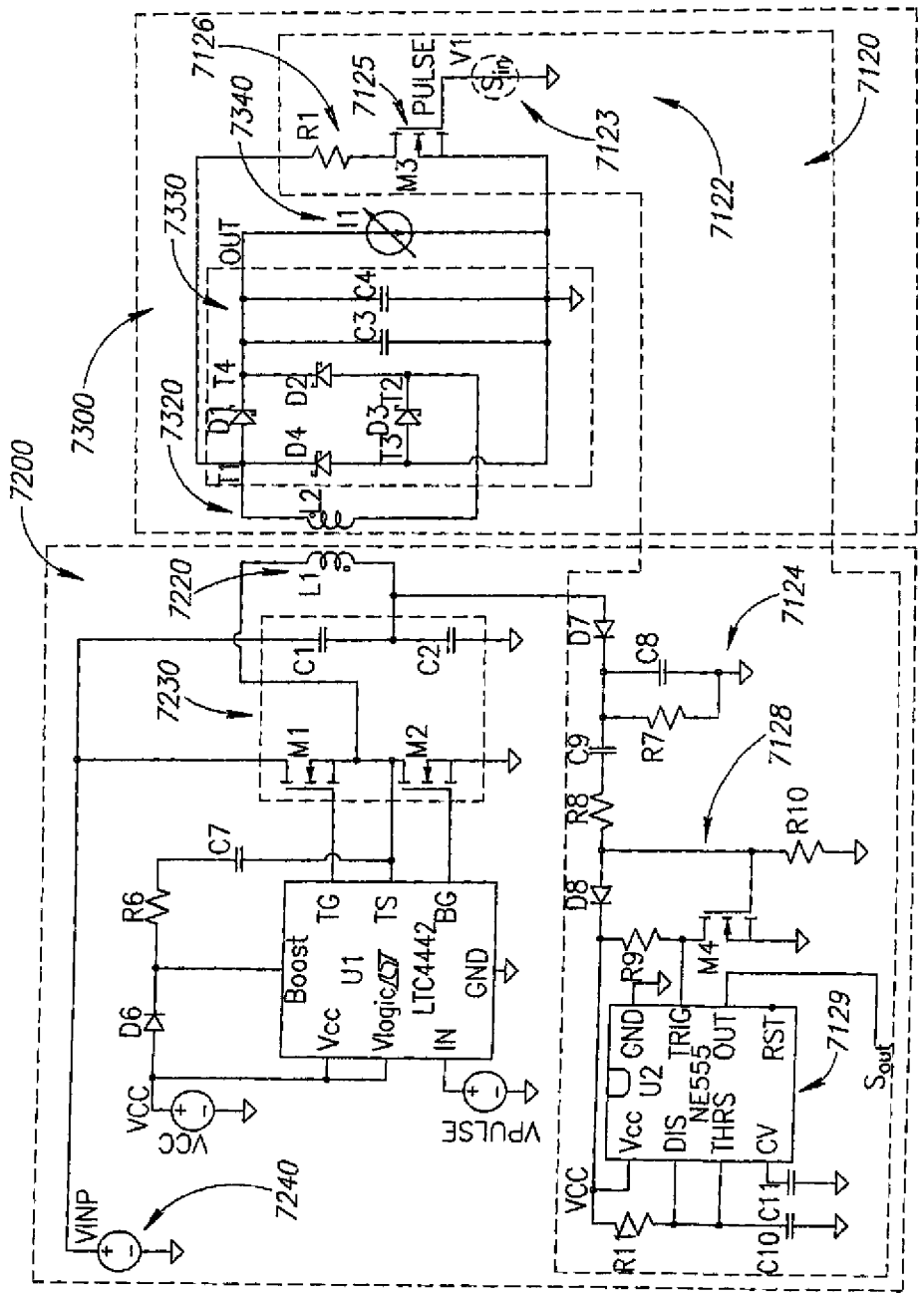
FIG. 16A is a circuit diagram of an inductive power transfer system including an inductive feedback channel for providing coil-to-coil signal transfer concurrently with uninterrupted inductive power transfer between the coils in accordance with yet another embodiment of the invention.

FIG. 16A shows an exemplary circuit diagram of an inductive power outlet 7200 and a secondary unit 7300, according to another embodiment of the invention. An inductive feedback channel 7120 is provided for transferring signals between the coils concurrently with uninterrupted inductive power transfer.

The inductive power outlet 7200 comprises a primary coil 7220 driven by a half-bridge converter 7230 connected to a power source 7240. The half-bridge converter 7230 is configured to drive the primary coil 7220 at a frequency higher than the resonant frequency of the system. The secondary unit 7300 comprises a secondary coil 7320 wired to the input terminals $T_1$, $T_2$ of a rectifier 7330, and an electric load 7340 wired to the output terminals $T_3$, $T_4$ of the rectifier 7330.

The inductive feedback channel 7120 comprises a transmission circuit 7122, in the secondary unit 7300 and a receiving circuit 7124 in the inductive power outlet 7200. The transmission circuit 7122 comprises an electrical resistor 7126 connected to the rectifier 7330 via a power MOSFET switch 7125. A modulator 7123 may provide an input signal $S_{in}$ to the power MOSFET 7125.

It is noted that in this embodiment the transmission circuit 7122 is wired to one input terminal $T_1$ and one output terminal $T_3$ of the rectifier 7330. This configuration is particularly advantageous as, even when the transmission circuit 7122 is connected; the resistor 7126 only draws power from the system during one half of the AC cycle, thereby significantly reducing power loss.

The receiving circuit 7124 includes a voltage peak detector 7128 that is configured to detect increases in the transmission voltage, and a demodulator 7129 for producing an output signal $S_{out}$.

Figure 16B:
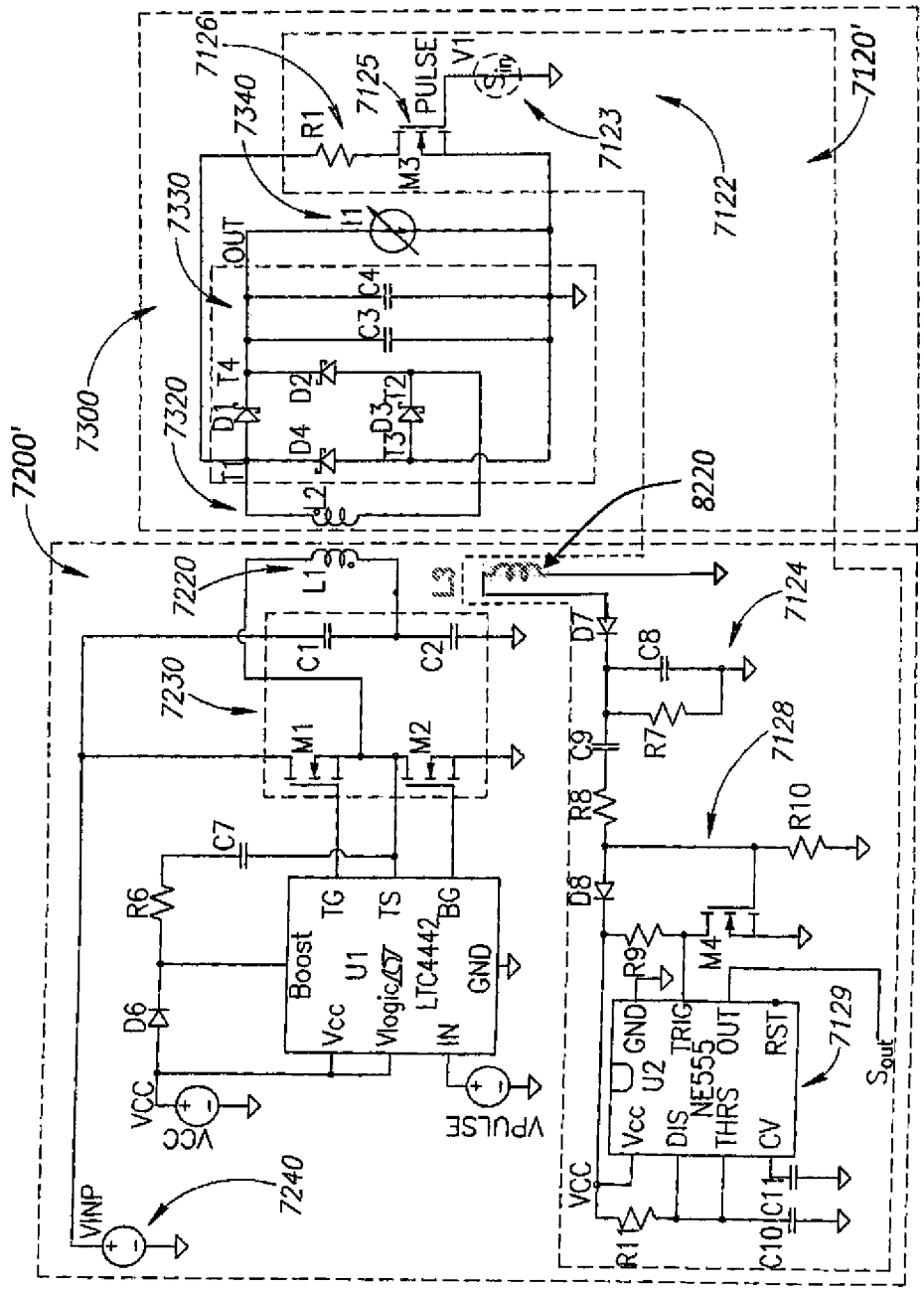
FIG. 16B is a circuit diagram of another inductive power transfer system including an inductive feedback channel including an auxiliary pickup coil for providing signal transfer.

Referring now to FIG. 16B, is another circuit diagram exemplary showing an inductive power outlet 7200' and a secondary unit 7300, according to an alternative embodiment of the invention. An alternative inductive feedback channel 7120' may include an additional pickup inductor L3 for receiving feedback signals. It is noted that such a pickup coil may comprise an auxiliary coil 8220 which is not electrically connected to the power transmission circuit.

The pickup coil may serve as a magnetic probe operable to detect fluctuations in the magnetic field in the vicinity of the primary and secondary inductors of the inductive couple. The magnetic probe may be connected to a signal detector such as a receiving circuit configured to detect feedback signals encoded in the magnetic fluctuations. The signal detector may be configured to produce an output signal which may be used to provide operating feedback to the driving circuit, for example by providing instructions to adjust transmission parameters for example to shift transmission frequency up or down to adjust output power. Alternatively, the feedback signals may be used communicate other data such as operating parameters from the inductive receiver to the inductive transmitter.

Where required one or more auxiliary coils 8220 may be incorporated into an inductive power transmitter, possibly adjacent to the primary inductive coil and operable to pick up feedback signals.

Accordingly, data generated in the inductive power receiver may be decrypted in the inductive power transmitter. In some embodiments, the use of an external (external to the power path) coil may provide better filtering. For example, the independent coil may be connected on both sides simultaneously to some filter whereas the power path may have restricted connections.

Furthermore the external coil may allow filtering of finer parameters, such as operating frequency even before power transfer and perhaps allowing more levels of data etc.

It may also be possible to use multiple pickup coils and thus allow the capturing of data when the inductive power receiver is laterally misaligned. Different coils can pick up data from different locations. This may improve data channel at misalignment. The different data from the different coils can be added by some analog circuits.

Figure 17:
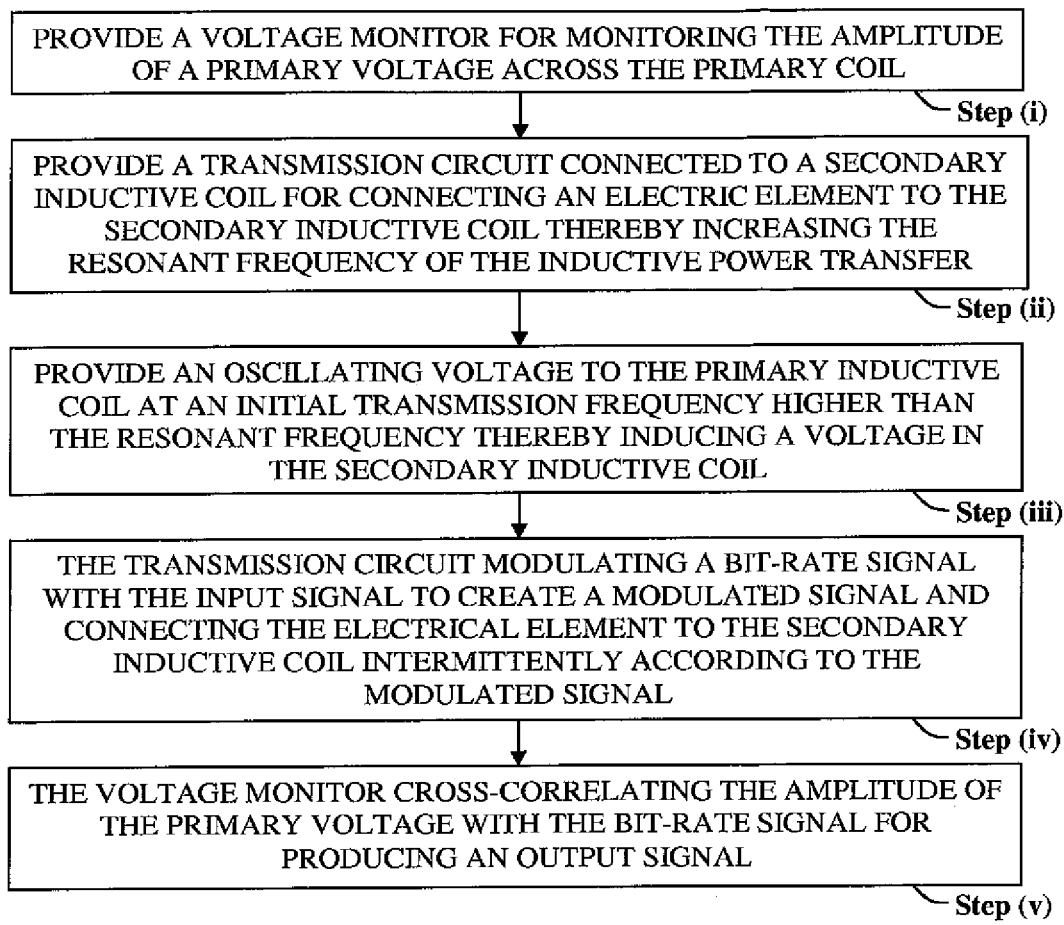
FIG. 17 is a flowchart showing a method for inductively transferring a signal from the secondary inductive coil to a primary inductive coil of an inductive power transfer system according to still a further embodiment of the invention.

With reference now to FIG. 17, a flowchart is presented showing the main steps in a method for transferring a signal from the secondary inductive coil to a primary inductive coil of an inductive power transfer system. The method includes the following steps:

Step (i)—connecting the primary inductive coil to a voltage monitor for monitoring the amplitude of a primary voltage across the primary coil;

Step (ii)—connecting the secondary inductive coil to a transmission circuit for selectively increasing the resonant frequency of the inductive power transfer system;

Step (iii)—providing an oscillating voltage to the primary inductive coil at an initial transmission frequency higher than the resonant frequency thereby inducing a voltage in the secondary inductive coil;

Step (iv)—using the transmission circuit to modulate a bit-rate signal with the input signal to create a modulated signal and connecting the electrical element to the secondary inductive coil intermittently according to the modulated signal, and Step (v)—using the voltage monitor to cross-correlate the amplitude of the primary voltage with the bit-rate signal for producing an output signal.

Therefore, the inductive communication channel 2120 may be used to transfer a feedback signal from the secondary inductive coil to the primary inductive coil for regulating power transfer across an inductive power coupling as described above.

It will be appreciated that embodiments of the present invention may be useful in a wide range of applications. Inductive power receivers may be used to wirelessly provide power for a variety of electrical devices. Embodiments of the present invention may be integrated into such inductive power receivers. In particular, because non-resonant transmission uses lower transmission voltages, heat loss from the non-resonant system is lower. Thus embodiments of the current invention may be of particular use when incorporated within high power applications such as power tools, kitchen appliances, bathroom appliances, computers, media players, office equipment and the like.

The reduced heat loss, associated with embodiments of the non-resonant systems of the invention, is particularly useful when heat dissipation is difficult for example when power receiver has small dimensions or for heat-sensitive equipment such as measuring devices. Also, it is desirable that devices implanted into a living body do not dissipate large amounts of heat into the body. Therefore, non-resonant inductive transfer is well suited to implanted devices, such as pace makers, trackers and the like.

It is also noted that in recent years public concern about the threat of a global energy crisis has resulted in a greater emphasis being placed upon optimizing the efficiency of energy transfer. It is difficult to achieve more demanding specifications using existing technology and, in this context, embodiments of the present invention may be used to provide high powers with very low energy losses. Consequently the current invention is an important element in the drive for greater efficiency.

Furthermore embodiments of the present invention may be advantageously utilized in inductive power transfer systems in any of the various applications in which power is transferred from a primary coil to a remote secondary coil. Amongst others, such applications include:

inductive chargers for use charging electronic devices,
inductive power adaptors for powering electronic devices such as computers, televisions, kitchen appliances, office equipment and the like,
medical applications in which power is transferred remotely to devices implanted in a patient,
communications with remote RFID tags,
military application in which power is transferred across thick armored plating,
communication or inductive energy transfer to secondary inductive coils buried underground.
communication or inductive energy transfer to secondary inductive coils submerged under water, for example in submarine applications, and
communication or inductive energy with secondary coils which are moving relative to the primary coil.

Thus, by using a transmission voltage oscillating at a frequency different from the resonant frequency of the system, the inductive transfer system has a higher tolerance to environmental fluctuations and variations in inductive coil alignment than other transfer systems and the frequency may be used to regulate power transfer. Moreover, when the transmission frequency is higher than the resonant frequency of the system, a peak detector may be used to indicate hazards and provide an inductive communication channel.

When two parameters are used (that is the resonance frequency and decay values or their equivalent, and their derived parameters the inductance and resistance), each receiver type may be associated with a range within the two dimensional parameter space. Thus, the chances of mistakenly identifying a foreign object or a defective, altered or misaligned reviver as a well-placed are reduced.

Optionally, if the assessed parameters ware found to change, but differ from any parameters set in the list, a warning signal may be issued 830. Warning signal may be an audio signal such as a beep or recorded message, or a visual signal such as a light or a note on a display, or a combination of audio and visual signals. When alignment coils such as coils 720*a-c* are used, warning signal may include alignment instructions.

As used herein, the term "processor", "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects.

Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

This written description uses examples to disclose the various embodiments of the disclosure, including the best mode, and also to enable any person skilled in the art to practice the various embodiments of the disclosure, including making and using any devices or systems and performing any incorporated methods. The patentable scope of the various embodiments of the disclosure is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the disclosure.

The invention claimed is:

1. A triggerable power transmitter for power transmission comprising:
   a primary coil in the power transmitter configured to be inductively coupled to a secondary coil in a power receiver;
   a driver used to electrically drive the primary coil;
   a resistor connected in series with the primary coil, wherein said resistor is used to produce a signal that corresponds to current flowing through the primary coil, reflecting resonance properties of the primary coil;
   a bypass switch having a closed position and an open position, connected in parallel to the resistor; and
   a processor configured to set the switch to the open position in order to determine that coupling exists between the primary coil and the secondary coil based on the signal, and set the switch to the closed position for power transmission, wherein the processor controls the power transmission with the driver while coupling exists.

2. The triggerable power transmitter of claim 1, further comprising a probing coil operable to provide the processor with an analog signal reflecting resonance properties of the primary coil.

3. A method for utilizing the triggerable power transmitter of claim 1, for power transmission from the primary coil in the power transmitter to the inductively coupled secondary coil in the power receiver, the method comprising:
   periodically determining coupling existence between the primary coil and the secondary coil comprising:
      switching, by the processor, the bypass switch to the open position;
      electrically exciting the primary coil, by the driver; and
      measuring the signal that is reflecting resonance properties of the primary coil, wherein the resonance properties are indicative of coupling existence; and
   triggering power transmission upon the coupling existence comprising:
      switching the bypass switch to the closed position in order to bypass the resistor; and
      electrically exciting the primary coil, by the driver; for transmitting power to an inductively coupled secondary coil.

4. The method of claim 3, wherein said exciting the primary coil further comprises applying a short electric pulse to the primary coil.

5. The method of claim 3, wherein said determining coupling existence further comprises determining a change in a resonance frequency of said primary coil.

6. The method of claim 3, wherein said determining coupling existence further comprises determining a change in an effective resistance of the primary coil.

7. The method of claim 3, wherein said exciting the primary coil further comprises activating the driver at a power level that is significantly reduced compared to power levels used for driving the primary coil during power transmission.

8. The method of claim 7, wherein said exciting the primary coil at reduced power level further comprises exciting the primary coil with a plurality of frequencies and determining if the secondary coil comprises frequency assessment response of the primary coil.

* * * * *